United States Patent
Tarunina et al.

(10) Patent No.: US 11,473,053 B2
(45) Date of Patent: Oct. 18, 2022

(54) METHODS FOR PRODUCING CELLS OF THE HEMATOPOIETIC LINEAGE USING HYDROGEL ENCAPSULATION

(71) Applicant: PLASTICELL LIMITED, Stevenage (GB)

(72) Inventors: Marina Tarunina, Stevenage (GB); Cedric Humbert, Stevenage (GB); Shahzad Ali, Stevenage (GB); Yen Choo, Stevenage (GB); Aaron Tsu Tshen Chuang, Stevenage (GB); Dennis Saw, Stevenage (GB)

(73) Assignee: PLASTICELL LTD., Stevenage (GB)

( * ) Notice: Subject to any disclaimer, the term of this patent is extended or adjusted under 35 U.S.C. 154(b) by 57 days.

(21) Appl. No.: 16/669,650

(22) Filed: Oct. 31, 2019

(65) Prior Publication Data
US 2020/0115674 A1    Apr. 16, 2020

Related U.S. Application Data

(63) Continuation-in-part of application No. PCT/EP2018/061618, filed on May 4, 2018.

(30) Foreign Application Priority Data

May 4, 2017 (GB) .................... 1707143.2

(51) Int. Cl.
*C12N 5/00* (2006.01)
*C12N 5/078* (2010.01)
*C12N 11/10* (2006.01)

(52) U.S. Cl.
CPC ......... *C12N 5/0012* (2013.01); *C12N 5/0644* (2013.01); *C12N 11/10* (2013.01); *C12N 2500/90* (2013.01); *C12N 2501/125* (2013.01); *C12N 2501/145* (2013.01); *C12N 2501/155* (2013.01); *C12N 2501/165* (2013.01); *C12N 2501/2306* (2013.01); *C12N 2501/2309* (2013.01); *C12N 2501/26* (2013.01); *C12N 2501/91* (2013.01); *C12N 2501/999* (2013.01); *C12N 2506/02* (2013.01);

(Continued)

(58) Field of Classification Search
None
See application file for complete search history.

(56) References Cited

U.S. PATENT DOCUMENTS

2003/0119107 A1   6/2003   Dang et al.
2016/0333310 A1   11/2016  Giarratana et al.

FOREIGN PATENT DOCUMENTS

WO    2016/004068 A1    1/2016

OTHER PUBLICATIONS

Yuan, Yan; et al; "Novel alginate three-dimensional static and rotating culture systems for effective ex vivo amplification of human cord blood hematopoietic stem cells and in vivo functional analysis of amplified cells in NOD/SCID mice" Transfusion, 53, 2001-2011, 2013 (Year: 2013).*

(Continued)

*Primary Examiner* — David W Berke-Schlessel
(74) *Attorney, Agent, or Firm* — Duane Morris LLP; Thomas J. Kowalski; Deborah L. Lu

(57) ABSTRACT

A hydrogel capsule comprising a stem cell core that has been induced to differentiate into a hematopoietic lineage cell, and methods for the production of hematopoietic lineage cells from stem cells encapsulated in a hydrogel.

17 Claims, 13 Drawing Sheets

(52) U.S. Cl.
CPC ...... *C12N 2506/45* (2013.01); *C12N 2513/00* (2013.01); *C12N 2533/30* (2013.01)

(56) References Cited

OTHER PUBLICATIONS

Liu, Yang; et al; "Effects of encapsulated rabbit mesenchymal stem cells on ex vivo expansion of human umbilical cord blood hematopoietic stem/progenitor cells" Journal of Microencapsulation, 26, 130-142, 2009 (Year: 2009).*

Leisten, Isabelle; et al; "3D co-culture of hematopoietic stem and progenitor cells and mesenchymal stem cells in collagen scaffolds as a model of the hematopoietic niche" Biomaterials, 33, 1736-1747, 2012 (Year: 2012).*

Stephen M. Dang, et al., Controlled, Scalable Embryonic Stem Cell Differentiation Culture, Stem Cells (2004) vol. 22:275-282.

Iliana Fauzi, et al., Early Exposure of Murine Embryonic Stem Cells to Hematopoietic Cytokines Differentially Directs Definitive Erythropoiesis and Cardiomyogenesis in Alginate Hydrogel Three-Dimensional Cultures, Stem Cells and Development (2014) vol. 23, No. 22, p. 2720-2729.

Y. Yuan, et al., Ex Vivo Amplification of Human Hematopoietic Stem and Progenitor Cells in an Alginate Three-Dimensional Culture System, International Journal of Laboratory Hematology (2011) vol. 33, p. 516-525.

International Search Report and Written Opinion dated Jun. 25, 2018 issued in PCT/EP2018061618.

* cited by examiner

A. (i)

(ii)

B. (i)

(ii)

A.

B.

(i)

| Name | Other name | Specificity |
|---|---|---|
| CD31 | PECAM | Endothelial / Hematopoiesis |
| CD34 | | Hematopoiesis |
| CD144 | VE Cadherin | Endothelial |
| VEGFR2 | KDR and Flk1 | Endothelial / Embryonic Hematopoiesis |

(ii)

C.

(i)

(ii)

(iii)

(iv)

D.

E.

(i)

(ii)

F.

(i)

(ii).

(iii).

A.

(i)

(ii)

(iii)

(iv)

(iii)

(iv)

D.

(i)

(ii)

E.  (i) Static Well Culture  (ii) WAVE Bioreactor

A.

(i)

(ii)

B.

(i)

(ii)

C.

(i)

(ii)

(iii)

A.

B.

C.

METHODS FOR PRODUCING CELLS OF THE HEMATOPOIETIC LINEAGE USING HYDROGEL ENCAPSULATION

RELATED APPLICATIONS AND INCORPORATION BY REFERENCE

This application is a continuation-in-part application of international patent application Serial No. PCT/EP2018/061618 filed 4 May 2018, which published as PCT Publication No. WO 2018/202900 on 8 Nov. 2018, which claims benefit of GB patent application Serial No. 1707143.2 filed 4 May 2017.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

Pluripotent stem cells represent potentially unlimited resources for the production of a wide range of cells from hematopoietic lineages. These cells may be used for both research purposes as well as cell therapy applications. The present invention provides efficient, scalable, and reproducible induction strategies to drive hematopoietic differentiation from stem cells in culture. The cells are useful, inter alia, for the realization of pluripotent stem cell-derived therapies.

BACKGROUND OF THE INVENTION

Generation of a diverse range of hematopoietic cells using pluripotent stem cells has the potential to fulfil a variety of unmet clinical needs. One such need is to restore or replace populations of hematopoietic cells that are unable to perform their normal function, either due to depletion of cell numbers or dysfunction of one or more internal cellular processes. This may occur due to a genetic defect (Lawn et al., 1980, Hoban et al., 2015), autoimmune effects (Panitsas et al., 2004) or disease (Ray-Coquard et al, 2009) leading to development of conditions such as anaemia, thrombocytopenia, lymphocytopenia and NKD (NK cell deficiency). Anti-cancer treatments such as chemotherapy can also result in the depletion of hematopoietic stem cell populations as well as reducing their proliferative capacity (Wang et al., 2006). Another crucial unmet clinical need is within the blood transfusion market, where the lack of supply of donor-derived blood products for transfusions will remain a long-term challenge, due to increased demand from a rapidly ageing population, the relatively invasive nature of collection and donor-matching complications (Baxter-Lowe et al., 2009). A cell therapy that is able to provide sufficient quantities of functional blood cells from a pluripotent stem cell source would be able to address all of the challenges mentioned.

In addition, human haematopoietic development is poorly understood; mouse hematopoietic development is well understood in comparison (Parekh & Crooks 2013). In addition to applications for cell therapy, therefore, creating an ex vivo model for human hematopoietic development from an embryonic source would be invaluable in further understanding the progression of a host of genetic and congenital blood diseases, such as sickle cell anaemia and thalassemia.

Platelets represent one example of a hematopoietic cell type that can be produced by pluripotent stem cells for clinical applications. Platelets play a critical role in blood clotting and wound healing. In a number of conditions such as certain autoimmune diseases, or following interventions such as chemotherapy and organ-transplantation, life-threatening thrombocytopenia is treated with a transfusion of platelets sourced from allogeneic blood donations. However, in approximately 15% of patients, the repeated infusion of allogeneic platelets causes an immune response, leading to 'alloimmune platelet refractoriness' which is costly to treat and life threatening (Pavenski et al. 2013). This medical problem can be solved by using autologous platelets generated from the patients' own induced pluripotent stem cells (iPSCs). This will provide an indefinite supply of platelets for repeated treatments without risking immune rejection. Platelets are anuclear and there are well established separation methods so it is very unlikely any undifferentiated hiPSCs or wrongly differentiated cells could contaminate a platelet preparation.

Platelets are the products of terminally differentiated megakaryocytes. During maturation, megakaryocytes increase their ploidy through endoreduplication and develop a unique demarcation membrane system that plays a primary role in proplatelet (the precursors to platelets) formation and platelet release (Chang et al, 2007). Megakaryocytes are derived from multipotent hematopoietic stem cells (HSC), which in turn evolve from a multipotential hemogenic precursor cell during early stages of development. Proliferation, maturation and terminal differentiation of megakaryocytic progenitors is orchestrated by a complex cascade of signalling molecules that induces the action of specific transcription factors such as Gata1, Tal1, NF-E2.

To date, there have been a number of strategies used to carry out the differentiation of pluripotent stem cells into hematopoietic lineages ex vivo. The three commonly used methods are embryoid body (EB)-based differentiation (the three-dimensional model), differentiation on stromal layers and differentiation on extracellular matrices (ECM's). Three-dimensional differentiation remains the most widely used as it most accurately recapitulates in vivo cell-cell signaling (Bratt-Leal et al 2009; Pettinato et al, 2015), is the most amenable to large scale culture (Yirme et al., 2008, Carpenedo et. al., Pettinato et al., 2014, Oh et al., 2009) and is free of human and animal tissue co-culture. Comparatively, whilst efficiently promoting the differentiation of pluripotent stem cells into mature hematopoietic phenotypes (Choi et al., 2009), co-culture with stromal feeder layer such as OP9 cells remains a commercial challenge due to the lack of regulatory clarity regarding the suitability of animal or tumour-derived cells for GMP manufacture and human transplantation (Mallon et al., 2006). ECM coatings such as collagen IV are efficient in producing certain functional cell types, such as platelets (Feng et. al, 2004) however both human-derived and recombinant ECM proteins are prohibitively expensive for large-scale production and ECM-based protocols usually require low cell densities, which is a further barrier to scalability. For these reasons, three-dimensional embryoid body (EB)-based differentiation remains the most widely used method for early hematopoietic differentiation from pluripotent stem cells.

Induction of differentiation of pluripotent stem cells. Embryoid body (EB) formation is the primary method for promoting early differentiation from pluripotent stem cells. When EB formation is induced in pluripotent stem cells, all three germ layers can be clearly seen (Iskovitz-Elder et al., 2000). If these EB's are then placed into specific differentiation media, cells can be directed towards specific lineages at the expense of others. A wide range of clinically-relevant cell types have been derived in this manner, including hematopoietic cells (Chadwick et al., 2003), neural cells (Zhang et al., 2001) and cardiac cells (Lian et al., 2012).

Of the EB-based methods, the most traditional is the hanging drop method (developed for mouse pluripotent stem cells), whereby defined numbers of mouse pluripotent stem cells develop into EB's whilst placed in liquid droplets (Keller, 1995). One challenge associated with this method, however is that human pluripotent stem cells do not aggregate as efficiently as mouse cells (Watanabe et al., 2007). The issues associated with aggregating human pluripotent stem cells have been overcome using the spin-EB method. Here, a defined number of pluripotent stem cells are forced into aggregating in low attachment 96-well plates by means of centrifugation (Ng et al., 2005). However, scalability remains a challenge for this method as the number of generated EBs is limited by the number of wells used.

Alternatives to the three-dimensional system include the use of mouse stromal feeder cell layers as a growth surface. Whilst stromal layers are efficient in promoting hematopoietic differentiation (Choi et al., 2009), concerns remain over the lack of regulatory clarity as to the suitability of animal feeder-derived cells for GMP manufacture and human transplantation. Differentiating induced pluripotent stem cells on Collagen IV extracellular matrix has recently been shown be a viable alternative to both the embryoid body method and to culture on stromal layers (Feng et al., 2014). However, Collagen IV is human-derived and thus may be prohibitively expensive for large scale production. Scalability is also limited by the low seeding density required.

Differentiation of hESC and iPSC in alginate. In tissues, cells are organised in three-dimensional (3D) formations. However, because of ease and convenience most cell culture systems in vitro are in the form of two dimensional monolayers. Forcing cells to adapt to flat and rigid surfaces in 2D can alter cell metabolism and change or reduce functionality. 3D systems are more biologically relevant and physiologically accurate than 2D systems. The relative advantages of 3D culture systems, including a summary of the various 3D culture systems presently available, has been reviewed by Cornley (Drug Discovery World, winter 2013).

Alginate, extracted from harvested brown seaweeds, is a type of hydrogel that has been proven to provide a permissive 3D environment for cell cultivation. Since alginate microbeads were used for the first time in humans to deliver an artificial pancreas in the 1980s (Kim et al. 2013), the polymer has been used with a variety of different cell types both in vivo and in vitro (Calafiore et al. 2006; Read, Sorensen, et al. 2001; Khosravizadeh et al. 2014; Olderøy et al. 2014; Mhanna et al. 2014; Read, Farhadi, et al. 2001; Bidarra et al. 2010). Useful properties of alginate include its ability to make hydrogels at physiological conditions; its ability to dissolve gently allowing for easy cell retrieval; its transparency for microscopic evaluation; its gel pore network (facilitating nutrient and waste material diffusion); and its non-animal origin.

Numerous alginate-based biomedical products are currently in clinical trials in addition to those that have already received market authorisation. Clinical applications include wound healing (Barnett & Varley 1987), bone graft substitutes for spinal fusion (Fu et al. 2009), cell therapy (Bjerkvig et al. 2003), and augmentation of the left ventricle wall for patients with dilated cardiomyopathy (Yu et al. 2009).

There are several examples where alginate hydrogels have been used to differentiate hESC or iPSC into defined lineages. In one example, microcapsules were used to differentiate human ESCs into definitive endoderm in 3D and could have a further potential application for immune-isolation and prevention of teratoma formation from hESCs during transplantation (Chayosumrit et al, 2010). In another example, alginate encapsulated EB's were differentiated into functional hepatocytes. This technology can potentially allow for the development of scalable stem cell differentiation strategies for both bioartificial livers (Kinasiewicz et al. 2007) and hepatocyte transplantation (Jitraruch et al. 2014). Alginate encapsulation technology was also applied to the differentiation of embryonic stem (ES) cells into insulin-producing cells (Wang et al, 2009). The functionality of these cells was confirmed by their insulin production capability. Upon glucose challenge, the amount of insulin produced by alginate-encapsulated, differentiated cells was found to be significantly higher than that from cells derived using the conventional two-dimensional differentiation system.

Unlike mouse ES cells that easily form EB-like structures following encapsulation as single cells into alginate beads (MAGYAR et al. 2006), human ES and iPS cells survive, expand and differentiate in 3D alginate only after prolonged exposure to Rock inhibitor or in the presence of conditioned medium or feeder layer (Kim et al, 2013, Chayosumrit et al, 2010). Furthermore no protocols have been published to date where encapsulated hES or iPS cells have been promoted to differentiate into hematopoietic lineages.

Generation of Erythrocytes, Natural Killer (NK) cells, Megakaryocytes and Platelets from hES and hiPS cells In recent years, progress has been made towards the establishment of in vitro protocols for differentiating both human embryonic stem (ES) and human iPS cells into megakaryocytes and platelets (Takayama et al, 2010; Lu et al, 2011, Feng et al 2014). Whilst most of the recently developed protocols use serum-free media, they still incorporate the step of embryoid body (EB) formation or co-culture with stromal feeder cells for the induction of early stages of differentiation (Pick et al, 2013, Vanhee et al, 2015). Significant progress was made recently when the EB formation step was replaced by a stage where iPS cells were seeded onto collagen IV-coated plates in the presence of Rock inhibitor (Feng et al, 2014). However, two major challenges remain: (1) the generation of megakaryocytes and their platelet progeny from pluripotent stem cells is inefficient, costly and difficult to scale up, and (2) the functional capacity of platelets generated in vitro is reduced when compared to standard donor platelets. Several reports on in vitro platelet production systems documented that the capacity of platelet production from a single MK is limited to only 1-50 platelets per megakaryocyte (Ono et al., 2012; Takayama et al., 2008, 2010), compared to several thousand platelets from each megakaryocyte in vivo (Patel et al., 2005). Given that one dose of platelet concentrate used for transfusion contains around $10^{11}$ platelets, protocols for the in vitro production of megakaryocytes need to be further improved to become applicable for clinical use. One of the ways to address this issue was the establishment of stable, immortalised megakaryocyte progenitor cell lines that could potentially provide unlimited supplies of megakaryocytes and platelets (Nakamura et al, 2014). A similar outcome was achieved by transduction of hES and hiPS cells with transgenes encoding megakaryocyte-specific transcription factors that prolonged the megakaryocyte expansion stage up to 80 days and thereby increased efficiency of megakaryocyte production by up to 200,000 MK's per iPSC (Moreau et al, 2016).

Established protocols also exist for the differentiation of hES and hiPS cells into natural killer cells and erythrocytes in two-dimensional culture. The protocols and applications of the NK cells obtained has been reported in Woll et al. 2009, Knorr et al. 2013, and Ni et al. 2011. An efficient protocol for the differentiation of hES and hiPS cells into erythrocytes in two-dimensional feeder-free and serum-free culture has also been described (Olivier et al., 2016).

Citation or identification of any document in this application is not an admission that such document is available as prior art to the present invention.

SUMMARY OF THE INVENTION

Here Applicants present a method in which stem cells are encapsulated in hydrogel beads. In the appropriate serum free, feeder free and Rock inhibitor free media, encapsulated stem cells undergo simultaneous expansion and differentiation into hemogenic precursor cells that protrude from alginate. These hemogenic precursor cells further give rise to a variety of hematopoietic lineages.

In a first aspect of the invention, a hydrogel capsule which may comprise a stem cell core that has been induced to differentiate into a hematopoietic lineage cell is provided. Without wishing to be bound by theory, it is believed that encapsulation of the stem cell core promotes its survival by mimicking its natural three-dimensional environment in vivo.

Encapsulation also increases volumetric efficiency. The hydrogel capsules are able to occupy a larger proportion of the volume of any given vessel, compared to monolayer systems. As the lowest level of the vessel is filled with capsules, the capsules will begin to stack, thus creating a deep volume formed of progressive layers of capsules. Encapsulation also circumvents the seeding density limitations. Thus, the production of hematopoietic lineage cells from stem cells can be scaled up without introducing additional genetic modifications (with transgenes, oncogenes or mutations) by using alginate microcapsules for the derivation and expansion of hematopoietic progenitors.

The stem cell is induced to differentiate into a hematopoietic lineage cell so that useful hematopoietic cells can be produced, collected, and used. For example, the hematopoietic cells produced by practising the invention may be used in therapeutic or research applications.

Unexpectedly, when the inventors observed encapsulated stem cells that had been induced to differentiate into a hematopoietic lineage cell, it was found that precursor cells proliferate, expand, and extrude from the hydrogel, sometimes as aggregates. Initially, precursor cells proliferate and expand in the direction of the surface of the capsule, forming extruded structures that are still connected to the capsule. As expansion continues, the part of each structure still contained within the capsule forms a stalk-like component to which an aggregate-like component outside of the capsule is connected. During this process, some cells begin to fall from the capsule, entering the bulk culture medium. Precursor cells include cells such as hemogenic precursor cells, multipotent hematopoietic stem cells, and multipotent hematopoietic progenitor cells. The pluripotent stem cells in the stem cell core remain entrapped in the matrix of the hydrogel capsule.

A number of advantages flow from the extrusion of hematopoietic precursor cells. For example, this phenomenon results in self-segregation of hematopoietic precursor cells from the undifferentiated source cells in the stem cell core. Separation of the hematopoietic product is therefore simplified, and the risk of contamination is greatly reduced.

Further advantageously, it has been found that extruded cells continue to differentiate in the bulk medium, reaching mature stages of development. The process of differentiation is therefore synchronised at the various stages of extrusion. Pluripotent stem cells in the stem cell core remain trapped in the hydrogel matrix. Cells traversing the hydrogel matrix, cells forming aggregate at the surface of the hydrogel capsule, and fully extruded cells can be in early stages of differentiation (hemangioblasts, hemogenic precursors, hemogenic endothelium). Fully extruded cells in the bulk medium are in the later stages of differentiation, or are fully mature (e.g. terminally differentiated).

Thus, in one embodiment, a hydrogel capsule may comprise a stem cell core that has been induced to differentiate into a hematopoietic lineage cell, wherein the hematopoietic lineage cell is extruding from the hydrogel capsule. In a preferred embodiment, the extruding or extruded cell is a hemogenic precursor cell. Most preferably, the extruding or extruded cell has been induced into definitive hematopoiesis.

In embodiments, the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

In embodiments, the stem cell core is a clump of stem cells or a spheroid. A clump of stem cells may be obtained by passaging a culture of cells mechanically or enzymatically. In embodiments, a clump of stem cells may be obtained by both mechanical and enzymatic passaging. For example, clumps or clusters of cells are obtained following treatment of a cell culture with Collagenase IV and mechanical disruption. Spheroids can be obtained by dissociating stem cells into single cell suspension and culturing on an orbital shaker. Preferably, the stem cells are cultured on an orbital shaker in a 3D stem cell culture medium, such as Cellartis DEF-CS 500 Xeno-Free 3D Spheroid Culture Medium.

In embodiments, the hydrogel used to form the hydrogel capsule may comprise an alginate.

In embodiments, the stem cell core has been induced to differentiate into a hematopoietic lineage cell by exposing the encapsulated stem cell core to a culture condition which promotes differentiation of the stem cell core into the hematopoietic lineage cell. Suitable culture conditions are disclosed herein, and others will be within the purview of the person skilled in the art.

In embodiments, the hydrogel encapsulated stem cell core that has been induced to differentiate into a hematopoietic lineage cell is stored for later use. For example, the encapsulated core may be rapidly frozen in storage medium shortly after induction of differentiation. This may allow for the long-term storage and transport of the induced encapsulated core. Such a frozen induced encapsulated core may then be primed for immediate production of hematopoietic lineage cells upon re-thawing.

In another aspect of the invention, a method for producing a hematopoietic lineage cell is provided. The method may comprise the steps of:

a) encapsulating a stem cell core in a hydrogel; and
b) exposing the encapsulated stem cell core to a culture condition which promotes differentiation of the stem cell core into the hematopoietic lineage cell.

In embodiments, the method further may comprise the steps of:

a) changing the culture condition to a different culture condition which further promotes differentiation of the stem cell into the hematopoietic lineage cell; and optionally
b) repeating step a) with further different culture conditions which further promote differentiation of the stem cell into the hematopoietic lineage cell.

In other words, a stem cell core is encapsulated in a hydrogel capsule and exposed to a number of different culture conditions in succession until the desired hematopoietic lineage cell is obtained. Usually, the encapsulated stem cell core is exposed to an initial culture condition and then at least one other culture condition, different to the initial culture condition.

The sequence of changing culturing conditions is known as a protocol. Different protocols have been and can be developed. Amongst other things, different protocols can direct stem cells to develop along specific cell lineages and to produce specific cell types. For example, one of the protocols disclosed herein directs stem cell development to produce megakaryocytes, whilst another protocol directs stem cell development to produce macrophages.

To develop efficient protocols for differentiation of pluripotent stem cells into the hematopoietic lineage, the combinatorial screening platform CombiCult® was used. Combicult® is a high throughput, bead-based combinatorial cell culture technology which allows the user to assay multiple combinations of media compositions in sequential steps simultaneously in small volumes (Choo 2002, Choo 2008, Tarunina et al, 2014). As suspension cells do not adhere well to standard microcarriers it was necessary to "entrap" cells inside alginate beads which could then be shuffled between the different media conditions and labelled with fluorescent tags. A method for labelling of microencapsulated cell cores with fluorescent tags was incorporated into the CombiCult screening platform (Choo 2011, Tarunina et al, 2016). This second generation CombiCult system was used to discover protocols that promote the differentiation of pluripotent (e.g. hES and hiPS) stem cells into mature hematopoietic cells. CombiCult allows for the screening of several iPS/ES cell lines simultaneously, leading to the discovery of protocols that work efficiently across a broad range of cell lines as well as protocols preferred by individual cell lines. In these protocols the first stages of differentiation from pluripotent stem cells into early hematopoietic progenitors take place inside of alginate beads therefore replacing the requirement for embryoid body formation, stromal feeder layer or ECM. The original Combicult method is described in international patent application publication number WO 2004031369 A1, and in European patent publication number EP 1551954 B1. The second generation Combicult method is described in international patent application publication number WO 2011/047870 A1, and in European patent application publication number EP 2491386 A1.

Furthermore at the next stage of differentiation, rapidly expanding hemogenic precursors extrude from alginate beads leaving behind cells that failed to differentiate correctly, thereby increasing the homogeneity of desired progenitors as well as synchronizing cells for further differentiation. Introduction of the alginate encapsulation step increased overall yield of hematopoietic cells, reduced the cost of hematopoietic cell manufacture and allows for the production of hematopoietic lineage cells from stem cells to be scaled up by transfer into large-scale suspension bioreactor systems.

In an embodiment of the method, the initial culture condition comprises a medium which may comprise:

a) a hematopoietic stem cell expansion medium; and
b) 50 ng/ml of each of BMP4, VEGF, and bFEF;

the first different culture condition comprises a medium which may comprise:

a) a hematopoietic stem cell expansion medium;
b) 10 ng/ml of each of BMP4, VEGF, and bFEF;
c) 284 µM ascorbic acid; and
d) 0.1 mM βME;

the second different culture condition comprises a medium which may comprise:

a) SFEM;
b) 50 ng/ml of each of TPO, SCF, and Flt3;
c) 20 ng/ml of IL6;
d) 10 ng/ml of IL9;
e) 5 U/ml of heparin; and
f) 10 µM of Valproic acid;

and the third different culture condition comprises a medium which may comprise:

a) SFEM;
b) 50 ng/ml of each of TPO and SCF;
c) 10 ng/ml of each of IL6 and IL9;
d) 5 µM of Arachidoic acid;
e) 0.5 µM of ETP; and
f) 2.5 mM nicotinamide.

In another embodiment of the method, the initial culture condition comprises a medium which may comprise:

a) a hematopoietic stem cell expansion medium; and
b) 50 ng/ml of each of BMP4, VEGF, and bFEF;

the first different culture condition comprises a medium which may comprise:

a) a hematopoietic stem cell expansion medium;
b) 50 ng/ml of each of BMP4 and VEGF;
c) 20 ng/ml of each of bFEF, TPO, and SCF; and
d) 10 µM Valproic acid;

the second different culture condition comprises a medium which may comprise:

a) a hematopoietic stem cell expansion medium;
b) 20 ng/ml of SCF;
c) 500 nM of Compound-P;
d) 100 nM of GPR40ag;
e) 2 mM of Metformin; and
f) 5 U/ml of heparin;

and the third different culture condition comprises a medium which may comprise:

a) SFEM;
b) 50 ng/ml of each of TPO and SCF;
c) 10 ng/ml of each of IL6 and IL9;
d) 5 µM of Arachidoic acid;
e) 0.5 µM of ETP; and
f) 2.5 mM nicotinamide.

The culture condition to which the encapsulated stem cell is exposed can be changed by methods that will be familiar to one skilled in the art. For example, where the culture condition is determined by the composition of the culture medium, the medium may be changed from one to another by removing the hydrogel capsules from the first (e.g. initial) medium, washing them in buffer, and placing them in the second (e.g. first different) medium.

Other suitable protocols are set forth in Table 1.

In embodiments, the culture condition may include temperature, pH, salinity, pneumostatic pressure, hydrostatic pressure, % $CO_2$, % $O_2$, % $N_2$, exposure to radiation, including infra-red, visible, or UV light, alpha, beta, or gamma radiation, or any combination thereof.

In embodiments, the hematopoietic stem cell expansion medium is STEMLINE II (Sigma).

In embodiments, the mature hematopoietic lineage cell obtained by the method is a megakaryocyte.

In embodiments, the mature hematopoietic lineage cell obtained by the method is a macrophage, such as an M1 or an M2 macrophage.

In embodiments, the day on which the encapsulated stem cell is exposed to the initial culture condition is day 1, and the encapsulated stem cell is exposed to the first different culture condition on day 3 or day 4, to the second different culture condition on day 7, and to the third different culture condition on day 11.

In embodiments, the method further includes the step of separating one or more hematopoietic lineage cells from the encapsulated stem cells. The separated cells may then be used, for example, in therapeutic or research applications. The cells may be subjected to further modifications and processing steps before they are used. Such will be determined by the particular application. Further processing steps may include enrichment, and the addition of stabilisers, antimicrobials, and/or other additives.

In embodiments of the method, at least one culture condition is feeder-free. In embodiments, all culture conditions are feeder-free. Other embodiments are envisaged wherein any number of culture conditions is feeder free, from only one, to substantially all, or all but one.

In embodiments of the method, at least one culture condition does not comprise any of a conditioned medium, serum, or a ROCK inhibitor. In embodiments, all culture conditions lack conditioned medium, serum, or a ROCK inhibitor. Other embodiments are envisaged wherein any number of culture conditions lack conditioned medium, serum, or a ROCK inhibitor, from only one, to substantially all, or all but one.

In embodiments of the method, the hydrogel may comprise an alginate.

In embodiments of the method, the stem cell core may be a spheroid or a clump.

Another aspect of the invention provides a composition which may comprise:

a) a hydrogel capsule which may comprise a stem cell; and b) a hematopoietic lineage cell.

In embodiments, the hematopoietic lineage cell is located outside of the hydrogel capsule.

In embodiments, the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

In another aspect, the invention provides a vessel, preferably a bioreactor, containing one or more hydrogel capsules according to the invention, or containing a composition according to the invention.

In another aspect, the invention provides for the use of a vessel according to the invention in a method for producing a hematopoietic lineage cell.

In embodiments, use of a vessel according to the invention is in a method also according to the invention.

Use of a vessel according to the invention, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

In another aspect of the invention, there is provided the use of a hydrogel capsule according to the invention in a method for producing a hematopoietic lineage cell.

In embodiments, the use of a hydrogel capsule according to the invention is in a method also according to the invention.

In embodiments of the use of a hydrogel capsule according to the invention, the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

In any embodiment or aspect of the invention, including the hydrogel capsule, the methods, the vessel, and the uses, the hematopoietic lineage cell may be a hemogenic precursor cell, a multipotent hematopoietic stem cell, a multipotent hematopoietic progenitor cell, a common myeloid progenitor, a common lymphoid progenitor, a megakaryocyte, a platelet, an erythroblast, an erythrocyte, a myeloblast, a basophil, a neutrophil, an eosinophil, a monocyte, a macrophage, a myeloid dendritic cell, a lymphoblast, a natural killer cell, a B lymphocyte, a T lymphocyte, a plasma cell, a lymphoid dendritic cell, or any cell of the hematopoietic lineage.

In any embodiment or aspect of the invention, including the hydrogel capsule, the methods, the vessel, and the uses, the stem cell type of the stem cell core may include, but is not limited to, an embryonic stem cell (ES cell or ESC), preferably a human embryonic stem cell (hES cell or hESC), an induced pluripotent stem cell (iPS cell or iPSC), preferably a human induced pluripotent stem cell (hiPS cell or hiPSC) including an episomal hiPS cell (ehiPSC), an adult stem cell (also known as a somatic stem cell), or umbilical cord blood-derived cells (CB-derived cells).

In contrast to the EB method, the hydrogel encapsulation method described here provides a novel way of initiating early hematopoietic differentiation of human pluripotent stem cells. There are a number of features that distinguish this method from those in the prior art. Firstly, the method is feeder-free and thus has no need for any animal derived products such as stromal layers. Also, hydrogels, such as alginate, are relatively inexpensive, particularly compared to human-derived or recombinant ECM proteins such as Collagen IV. Hydrogel encapsulation is more scalable than EB for hematopoietic cell manufacture as large numbers of hydrogel beads can be produced during a single encapsulation. These beads can then easily be transferred to a larger scale vessel for suspension culture, whereas EB formation can only occur in static plates (Itskovitz-Eldor et al., 2000; Ng et al., 2005). The early hematopoietic progenitors formed inside the beads can then be cryopreserved (Malpique et al. 2010) or used directly as a starting point for a variety of hematopoietic lineage differentiations (including, but not exclusive to T-cells, NK cells, red blood cells, granulocytes, megakaryocytes, macrophages, and monocytes).

A key feature of differentiation in alginate beads is that while the pluripotent stem cells remain inside the beads, aggregates of maturing cells extrude from the beads during differentiation and can be cultured in suspension outside of the alginate beads. This allows for simple separation of maturing cells from pluripotent stem cells which typically present clinical safety concern.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
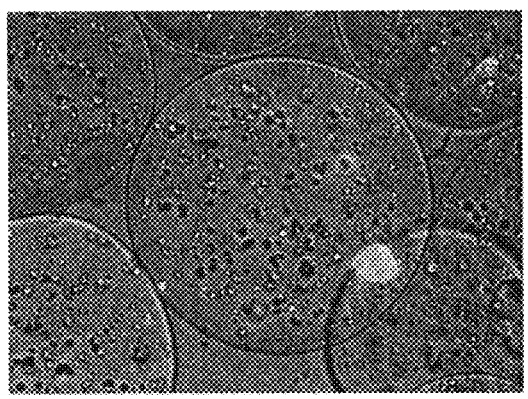
FIG. 1A-1B. Survival and hematopoietic differentiation of cells encapsulated in alginate beads: A. Viability staining of hiPS-SBi cells encapsulated as single cells (i) or clumps (ii) in alginate beads 10 days after encapsulation (Calcein AM staining). B. ICC staining of hiPS-SBi cells encapsulated as single cells (i) or clumps (ii) using Megakaryocyte specific antibodies CD41a and CD42b following 14 days of differentiation in alginate beads according to protocol #32.
Figure 1:
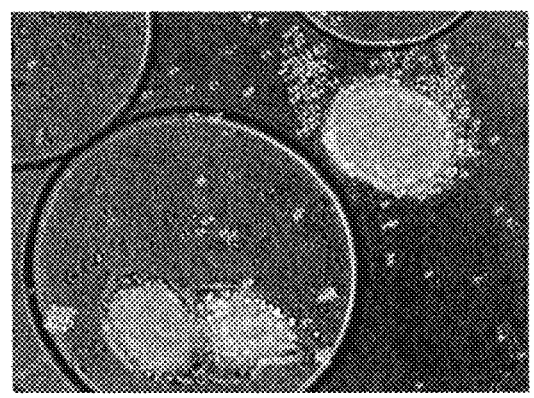
Figure 1:
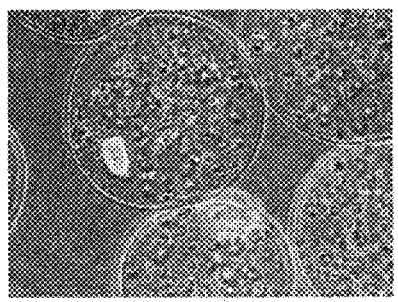
Figure 1:
Figure 1:
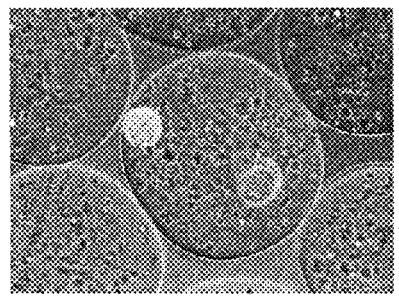
Figure 1:
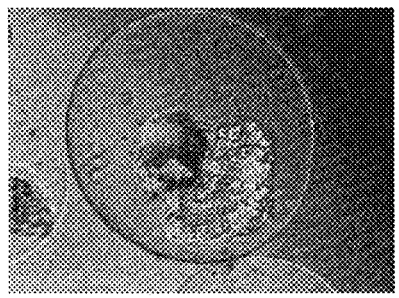

Unless defined otherwise, all technical and scientific terms used herein have the same meaning as commonly understood by those of ordinary skill in the art, such as in the arts of peptide chemistry, cell culture and phage display, nucleic acid chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.; Ausubel et al., Short Protocols in Molecular Biology (1999) 4th ed., John Wiley & Sons, Inc.), which are incorporated herein by reference.

Hydrogels which may be used in the invention include alginate, agarose, hyaluronic acid, poly(ethylene) glycol (PEG), poly(ethylene oxide), poly(vinyl alcohol), poly (acrylic acid), poly(propylene fumarate-co-ethylene glycol), self-assembled peptide, collagen, gelatin, collagen-gelatin, fibrin (fibrinogen-thrombin), fibroin, fibroin-gelatin, elastin-like polypeptide, chondroitin sulfate, dextran, chitosan, pectin, or fumarate hydrogels, though this list is not exhaustive. A hydrogel which may comprise a combination of two or more hydrogels may also be used.

A "capsule" is a protective barrier which contains a stem cell core. The term is commonly used in the art to refer to semi-permeable or impermeable structures; in the context of the present invention, capsules are semi-permeable and allow the passage of the components of growth media, growth factors, cytokines, chemokines, ions, nutrients, and other reagents. Furthermore, the material of the capsule allows differentiating cells to proliferate and expand within it, for example cells may proliferate and expand away from the stem cell core towards the surface of the capsule. In the case of a hydrogel capsule, differentiating cells proliferate and push through the hydrogel matrix. Microencapsulation, or encapsulation, is the enclosing of a cell core in a microcapsule. In a hydrogel capsule, the capsule material may comprise a hydrogel. A capsule may also be referred to as a "bead".

A "cell", as referred to herein, is defined as the smallest structural unit of an organism that is capable of independent functioning, or a single-celled organism, consisting of one or more nuclei, cytoplasm, and various organelles, all surrounded by a semipermeable cell membrane or cell wall. The cell may be prokaryotic, eukaryotic, animal or plant, or archaebacterial.

For example, the cell may be a eukaryotic cell. Mammalian cells are preferred, especially human cells. Cells may be natural or modified, such as by genetic manipulation or passaging in culture, to achieve desired properties.

A "stem cell" is a totipotent, pluripotent or multipotent cell capable of giving rise to more than one differentiated cell type. Stem cells may be differentiated in vitro to give rise to differentiated cells, which may themselves be multipotent, or may be terminally differentiated. Cells differentiated in vitro are cells which have been created artificially by exposing stem cells to one or more agents which promote cell differentiation.

A "totipotent" cell is a cell with the potential to differentiate into any type of somatic or germ cell found in the organism. Thus, any desired cell may be derived, by some means, from a totipotent cell.

A "pluripotent" cell, such as a pluripotent stem cell, is a cell which may differentiate into more than one, but not all, cell types.

As used herein, "stem cell" includes any totipotent, pluripotent, or multipotent cell capable of giving rise to cells of the hematopoietic lineage. Such cells include, but are not limited to, embryonic stem cells (ES cell or ESC), preferably human embryonic stem cells (hES cells or hESCs), induced pluripotent stem cells (iPS cells or iPSCs), preferably human induced pluripotent stem cells (hiPS cells or hiPSCs) including episomal hiPS cell (ehiPSCs), adult stem cells (also known as somatic stem cells), or umbilical cord blood-derived cells (CB-derived cells), hemogenic precursor cells (such as hemangioblasts and hemogenic endothelium cells), multipotent hematopoietic stem cells, and multipotent hematopoietic progenitor cells.

As used herein, the term "hemogenic precursor cell" includes hemangioblasts and hemogenic endothelium cells. Further description of hemogenic precursor cells can be found in Wang et al., "Derivation and Characterisation of hematopoietic cells from human embryonic stem cells", Human Embryonic Stem Cell Protocols, edited by Kursad Turksen, 2006, pp 179-200 and Pereira et al., Dev Cell. 2016 Mar. 7; 36(5): 525-539.

Therefore, some cell types may be a stem cell in one embodiment and a product cell (i.e. a hematopoietic lineage cell as used herein) in another embodiment. It will be apparent to one skilled in the art that in any particular embodiment, the cell produced by the methods disclosed herein must be of a differentiation state that is later than the differentiation state of the stem cell in the stem cell core.

A "stem cell core" may be a single stem cell or a group of stem cells. Preferably, the stem cell or cells in the stem cell core remain stably totipotent, pluripotent, or multipotent throughout the differentiation protocols described herein. The manner in which the stem cell core is obtained is not critical. However, some examples include stem cell clumps obtained by mechanical and/or enzymatic passaging, stem cell spheroids (which can be obtained by the culturing methods described and referenced herein), and dissociated stem cells in single-cell suspension. In the invention, the stem cell core is preferably immobilised in the matrix of a hydrogel capsule.

A cell ceases to be a part of the stem cell core when it has differentiated to a differentiation state different to the original stem cell in the stem cell core, i.e. it has progressed to the next stage along a particular cell lineage and exhibits the phenotype of a more mature cell.

In the art, the term passaging is used to refer to the transfer of cells in culture from one culture condition to another. As used herein, the term passaging may also refer to the mechanical and/or enzymatic disruption of a culture with the aim of separating the bulk culture into smaller clumps or clusters.

Mechanical passaging involves the use of a tool or implement to physically disturb a cell culture. For cells growing in a dish, this can include cutting the culture into sections. For example, the end of a syringe or needle can be inserted into the culture at the top of the dish and drawn down to the bottom of the dish through the culture to make a cut. Multiple such cuts can be made parallel to the first, from one side of the dish to the other. Subsequently, the process may be repeated starting from one side of the dish, making cuts through the culture to the other side. In this manner, a grid pattern of cuts can be achieved, with clumps of cells separated and isolated from each other by the cuts. Specialised tools are available to make multiple cuts at the same time, thus saving labour (An Introduction to Cell Maintenance—Thermo Fisher Scientific, Publication Part Number MAN0006676) and may also be automated (Joannides A. et al., Stem Cells. 2006 February; 24(2):230-5).

Enzymatic passaging involves the use of enzymes to disrupt a cell culture. For example, a cell culture can be treated with enzymes that target extracellular matrix, thus hydrolysing the strong linkages that cells form to one another. For example, collagenase can be used to disrupt collagen matrix. One suitable protocol is given in StemBook, Cambridge (Mass.): Harvard Stem Cell Institute; 2008-2012 Jun. 10.

"Cell differentiation" is the development of a cell from one cell type to a different cell type. For example, a bipotent, pluripotent or totipotent cell may differentiate into a neural cell. Differentiation may be accompanied by proliferation, or may be independent thereof. The term 'differentiation' generally refers to the acquisition of a phenotype of a mature cell type from a less developmentally defined cell type, e.g. a neuron, or a lymphocyte, but does not preclude transdifferentiation, whereby one mature cell type may convert to another mature cell type e. g. a neuron to a lymphocyte.

The "differentiation state" of a cell is the level to which a cell has differentiated along a particular pathway or lineage.

As used herein, "induced to differentiate" means that a stem cell has been contacted with a culture condition directing it to begin producing differentiated cells of a particular lineage (e.g. hematopoietic), and that stem cell has begun a process of cellular division that will result in at least one daughter cell exhibiting a differentiated phenotype, e.g. a progenitor.

Cells of the hematopoietic lineage include the hemogenic precursor cell, the multipotent hematopoietic stem cell, the multipotent hematopoietic progenitor cell, the common myeloid progenitor, the common lymphoid progenitor, the megakaryocyte, the platelet, the erythroblast, the erythrocyte, the myeloblast, the basophil, the neutrophil, the eosinophil, the monocyte, the macrophage, the myeloid dendritic cell, the lymphoblast, the natural killer cell, the B lymphocyte, the T lymphocyte, the plasma cell, and the lymphoid dendritic cell.

A cell is "extruding" from a hydrogel capsule when it has left the cell core and is pushing through the hydrogel as proliferating cells expand. The term "extruding" also describes the exit of cells from the hydrogel matrix, and the formation of cell stalks or aggregates within the matrix or at the outer surface of the hydrogel. Cells exiting the matrix can be considered to extrude, and cells that have exited the matrix (i.e. they are outside of the hydrogel capsule) can be considered to have extruded. Extruding cells may be of any type and may be at any stage of differentiation, but preferably extruding cells are not pluripotent stem cells. Most preferably, extruding cells are not stem cells of the stem cell core.

Multi-planar cell sheets or a spherical cell colony. A type of 3D culture resembling a sphere. Spheroids can be generated with or without a scaffold, for example in a capsule, such as a hydrogel capsule (e.g. Lei and Schaffer, 2013). Culture of spheroids can be supported by a bespoke 3D culture medium. A 3D culture is an in vitro culture of cells that has been artificially manipulated to grow in three dimensions, creating an environment that more closely reflects the cells' natural in vivo environment, and thus encouraging the cells to adopt more natural behaviours than would be achieved by a traditional two-dimensional surface culture. Such 3D cultures encourage interactions between cells to maximise cell-cell interaction by self-generated ECM. Scaffold-free methods enable the self-assembly of cells into organised 3D structures.

As used herein, the term "culture condition" refers to the environment which cells are placed in or are exposed to in order to promote growth or differentiation of said cells. Thus, the term refers to the medium, temperature, atmospheric conditions, substrate, stirring conditions and the like which may affect the growth and/or differentiation of cells. More particularly, the term refers to specific agents which may be incorporated into culture media and which may influence the growth and/or differentiation of cells.

A cell is "exposed to culture conditions" when it is placed in contact with a medium, or grown under conditions which affect one or more cellular process(es) such as the growth, differentiation, or metabolic state of the cell.

Thus, if the culture conditions comprise culturing the cell in a medium, the cell is placed in the medium for a sufficient period of time for it to have an effect. Likewise, if the conditions are temperature conditions, the cells are cultured at the desired temperature.

ABBREVIATIONS, ACRONYMS, TRADE NAMES bFGF: basic fibroblast growth factor
BMP4: Bone morphogenic protein 4
BSA: Bovine serum albumin
Compound P: PPARg agonist L-165,041
DMEM: Dulbecco's modified eagle medium
DPBS: Dulbecco's phosphate buffered saline
ehiPS: episomal human induced pluripotent stem cell
EPO: Erythropoietin
Essential 8 media: from ThermoFisher Scientific
ETP Eltrombopag (SB-497115-GR)—TPO receptor agonist
FCS: fetal calf serum
FGF: fibroblast growth factor
FGF2: basic fibroblast growth factor
FLT3: fms-like tyrosine kinase 3
GMP: Good Manufacturing Practice
GPR40: Free fatty acid receptor 1
GPR40ag: Free fatty acid receptor agonist 1—CAS 885101-89-3
Hoescht: Hoescht nuclear stain
KO-DMEM: KnockOut Dulbecco's Modified Eagle Medium (ThermoFisher)
LDL: low density lipoprotein
MEF: Mouse embryonic fibroblast
NEAA: non-essential amino acids
OP9 cells: Stromal feeder layer PBS: Phosphate buffered Saline
PE: Phycoerythrin
PF4: Platelet factor 4
PFA: Paraformaldehyde
PGE: Prostaglandin E
ROCK Rho-associated, coiled-coil containing protein kinase
SBI/SBi: iPS cell line from System Biosciences Inc.
SCF: Stem cell factor
SFEM: Serum-free expansion medium
STEMLINE (II): Hematopoietic Stem Cell Expansion Medium (Sigma)
TPO: Thrombopoietin
TRAP: Thrombin receptor activator peptide
Tyrode buffer: Tyrode's Salt solution (Sigma 2397)
VEGF: Vascular endothelial growth factor
CB: Umbilical cord blood The source of cells for the stem cell core may be any of the types of stem cell disclosed herein. Such cells include embryonic stem cells (ES cell or ESC), preferably human embryonic stem cells (hES cells or hESCs), induced pluripotent stem cells (iPS cells or iPSCs), preferably human induced pluripotent stem cells (hiPS cells or hiPSCs) including episomal hiPS cell (ehiPSCs), adult stem cells (also known as somatic stem cells), or umbilical cord blood-derived cells (CB-derived cells), hemogenic precursor cells, multipotent hematopoietic stem cells, and multipotent hematopoietic progenitor cells.

Adult stem cells are undifferentiated cells, e.g. pluripotent or multipotent cells, found amongst mature, developed, and differentiated tissues. They can be found in both adults and children. In the broadest sense, adult stem cells are any totipotent, multipotent, or pluripotent stem cell derived from non-embryonic tissue. Adult stem cells include hematopoietic stem cells, mesenchymal stem cells. Hematopoietic stem cells are found in, and can be isolated from, bone marrow as well as umbilical cord blood. Mesenchymal stem cells are found in and can be isolated from placenta, adipose tissue, lung, bone marrow, and blood.

Yuan et al. describe the expansion of cord blood cells in an alginate three-dimensional culture system (Int J Lab Hematol. 2011 October; 33(5):516-25). However, after expansion, the undifferentiated cord blood cells were released from the alginate and transferred to a conventional differentiation protocol.

Stem cell cores can be obtained by methods known in the art. Typically, stem cells are grown in culture, but their proliferation is managed to retain pluripotency and prevent differentiation. This can be achieved by passaging the cells mechanically or enzymatically. Mechanical passaging typically yields clumps of stem cells. These clumps may then be encapsulated and thus form the stem cell core of the invention. Enzymatic passaging can yield single stem cells. Single human pluripotent stem cells may be less suitable as stem cell cores of the invention because they have low viability in alginate and had been shown to produce a lower yield of mature cells.

The clump size is not critical to the functioning of the invention. The size of any clump obtained by passaging methods in the art is suitable for performing the function of the stem cell core of the invention. As an example, a cell clump which may comprise from about 50 to about 200 stem cells may be obtained by passaging and used as the stem cell core of the invention. Preferably, the cell clump may comprise from 100 to 150 stem cells.

Methods for growing spheroids are known in the art. The exact method by which spheroids are obtained is not critical to the invention. One preferred method is described in Example 4. One reason that the method described in Example 4 is preferred is that it is easy to scale up for large scale production of spheroids for use as stem cell cores of the invention. Generally, this method involves dissociating a culture of stem cells into single cell suspension before culturing cells individually and separately on an orbital shaker. Within the first 24 hours of suspension culture, stem cells form small aggregates (spheroids) and single cells that fail to do so are discarded. The culture is preferably supported by a 3D culture medium. The DEF-CS 500 Xeno-Free 3D Spheroid Culture Medium available from Takara Bio (US) has proven to be an adequate culture medium for this purpose. This medium comprises a basal medium (DEF-CS 500 Xeno-Free Basal Media) supplemented with DEF-CS Xeno-Free 3D Spheroid Additives (Additives 1-3). Additive 2 has proven to have the greatest positive effect on spheroid formation.

Alternative methods for generating iPSC spheroids exist. For example a kit and appropriate media to grow hiPS cells in spheroid culture are commercially available from Stemgent. In another system, spheroids can be formed and grown in thermos-responsive hydrogel (Lei & Schaffer, 2013). Microfluidic technology can also be applied to generate even size MSC spheroids (Vadivelu et al, 2017). Vadivelu et al. (2017) also review conventional methods for spheroid generation.

The number of stem cells in a spheroid may be similar to the number of stem cells in a passaged clump, as discussed above.

Once the stem cell core has been obtained, for example as a clump from passaging or as a spheroid, it may be encapsulated. Multiple cell encapsulation methods are known in the art and any may be used to encapsulate the stem cell core of the invention. Some suitable cell encapsulation methods are outlined below.

The stem cell cores of the invention are encapsulated in hydrogel capsules (or beads). Various types of soft and elastic hydrogels (with a typical aqueous media content of 98-99%) can be formulated at physiological conditions and allow cell culture in 3D without affecting cell viability and/or function. Types of hydrogel that have been used to encapsulate cells for culture include agarose (Kumachev et al., Biomaterials. 2011 February; 32(6):1477-83), hyaluronic acid (Ma et al., Biomat Sci. issue 11, 2014; Bae et al., Biotechnol Prog. 2006 January-February; 22(1):297-302), poly(ethylene) glycol (PEG) (Bakaic et al., RSC Advances, issue 45, 2015; Allazzetta et al., Small, Volume 11, Issue 42, pages 5647-5656, Nov. 11, 2015), self-assembled peptide (Tsuda et al., Langmuir. 2010 Feb. 16; 26(4):2645-9), collagen (Yeung et al., PLOS one, Dec. 14, 2015), collagen-gelatin (Ma et al. J. Mat Chem B, Issue 38, 2013), fibrin (fibrinogen-thrombin) (Yuan Ye et al., J Vis Exp. 2011 Sep. 19; (55). pii: 3251), elastin-like polypeptide (Bandiera, Expert Opinion on Drug Delivery, Vol. 14, pp. 37-48, 2017), chondroitin sulfate (Lim et al., Acta Biomater. 2011 Mar. 1; 7(3): 986-995), and fumarate (He et al., Biomacromolecules. 2007 March; 8(3):780-92). The development and biomedical applications of hydrogels are explored in Chirani N, Yahia L H, Gritsch L, et al. (J Biomedical Sci. 2016, 4:2) and in Caló et al. (European Polymer Journal 65, 2015, 252-267).

Preferably, the hydrogels used in the invention have no significant detrimental effect on cell survival and do not trigger any undesirable responses. Synthetic materials capable of forming hydrogels suitable for use in the invention include poly(ethylene oxide), poly(vinyl alcohol), poly (acrylic acid), polypropylene fumarate-co-ethylene glycol), and polypeptides. Agarose, alginate, chitosan, collagen, fibrin, gelatin, dextran, pectin and hyaluronic acid are naturally derived polymers that could also be used for this purpose (Caló and Khutoryanskiy, 2015).

Dextran: Dextran is natural polysaccharide obtained from the digestion of amylopectin. Yunxiao and collaborators created a copolymer between methacrylate-aldehyde-bifunctionalized dextran (DEXMA-AD) and gelatin B. Researchers demonstrated that this kind of hydrogel could promote adhesion of vascular endothelial cells (Massia et al, 2000, Biomaterials, 21: 2253-2261).

Gelatin: Gelatin is the denatured form of collagen, one of the major components of ECM. In its natural form it is water soluble but it can be crosslinked to obtain a hydrogel with higher mechanical properties and degradation rate (Chirani et al, 2016). Das and collaborators created two kinds of fibroin-gelatin hydrogels. One crosslinked by sonication was better for osteogenic differentiation while tyrosinased-gelatin-fibroin hydrogel supported better chondrogenic and adipogenic differentiation (Das et al, 2015, Acta Biomater 11: 233-246).

Chitosan: Chitosan is a polysaccharide from chitin of the crustacean skeleton. It is composed by the repetition of N-glucosamine units. In one study chitosan has been coupled with gelatin to create gel for cell seeding and drug delivery (Jiang et al., 2014, Acta Biomater 10: 1632-1645).

Hyaluronic acid: Hyaluronic Acid—HA is a Glycosaminoglycan GAG enclosed in the natural ECM, core of the material is a polysaccharide with high affinity for water. Hyaluronic acid (HA) hydrogel beads were prepared by photopolymerization of methacrylated HA and N-vinylpyrrolidone using alginate as a temporal spherical mold and used for encapsulation and tissue delivery of bovine articular chondrocytes (Bae et al, 2006, Biotechnol Prog. January-February; 22(1):297-302).

Pectin: Another polysaccharide used in tissue engineering hydrogels is pectin. It is obtained from cell walls after a low pH, high temperature processing. Unfortunately, until now, researchers have not reached the goal to standardize this product in an economically sustainable way (Chirani N, Yahia L H, Gritsch L, et al. (J Biomedical Sci. 2016, 4:2)

Alginate: Derived from brown algae, alginate is a polysaccharide composed of beta-D-mannuronic acid and alfa-L-gluronic acid. Its reticulation can also occur by divalent cations (Ca2+, Fe2+, Ba2+) (Shteyer et al, 2014, ActaBiomater, 10: 3209-3216).

In European patent EP 1 664 168 B1, a biodegradable unsaturated polymer, a crosslinking agent, and a porogen which may comprise biodegradable hydrogel are mixed together and allowed to form a porous scaffold in a mold or in a body cavity. Example biodegradable unsaturated polymers include poly(propylene fumarate) and poly(ε-caprolactone-fumarate). Example hydrogels include uncrosslinked or crosslinked collagen, an uncrosslinked or crosslinked collagen derivative (such as gelatin), and an uncrosslinked or crosslinked synthetic biodegradable polymer such as oligo(poly(ethylene glycol) fumarate).

U.S. Pat. No. 8,039,258 B2 discloses a tissue engineering scaffold containing self-assembling peptide hydrogels. A commercially available self-assembling peptide is 'PURAMATRIX' (3-D Matrix, Inc., Cambridge, Mass.), which has the sequence NH2-RADARADARADARADA-COOH US patent application publication number 2013/0236971 A1 discloses hydrogel scaffolds composed of synthetic terpolymers complexed with polyvinyl alcohol (PVA), which facilitate cell-sheet and tissue growth.

U.S. Pat. No. 6,379,690 B2 discloses a keratin-based hydrogel for biomedical applications and method for its production.

U.S. Pat. No. 8,592,574 B2 discloses the formation of beta-glucan-based hydrogel scaffold using radiation fusion. Beta-glucan dissolved in distilled water is irradiated with electron, gamma, or UV beams to form a gel. The gel facilitates cell attachment and makes it easy to create a biomimetic environment conducive to the growth and differentiation of stem cells.

It has been shown that a combination of different types of hydrogels can promote the switch from pluripotency to differentiation and influence lineage specification of stem cells (Dixon et al., PNAS, vol. 111:15, pp. 5580-5).

Encapsulation may be performed using any suitable technique. Microcapsule technology has been described, for example in U.S. Pat. Nos. 6,808,882 and 7,138,233 which describe emulsion microencapsulation technology in particular, but also set forth other microencapsulation methods at least some of which are suitable for encapsulating living cells.

Particular methods for encapsulating living cells have been described for immunoprotection of transplanted cells. For example, see Orive et al., (2203) Nature Medicine 9:104-107 and references cited therein.

In further embodiments, encapsulation can be performed under microfluidic control. The formation droplets containing cells in microfluidic systems has been widely demonstrated and has been used for high throughput droplet based assays (J. Clausell-Tormos, et al., Chemistry and Biology, 2008, 15, 5, 427) and cell sorting (J-C. Baret, et al., Lab Chip, 2009, 9, 1850). In these examples cells are encapsulated within water droplets separated by an oil phase. The water droplets are stabilised by a surfactant layer. Microfluidics systems can be scaled up by using multiple devices in parallel or in series.

The formation of hydrogel encapsulated cells has moreover been demonstrated using several methods. These include the formation of both alginate/cell water droplets and CaCl2 containing water droplets within an oil phase. When the two types of droplets fuse together, a cell-containing cross-linked hydrogel bead is formed as shown in FIG. 1 of H. Shintaku, et al., Microsystems Technology, 2007, 13, 951, reproduced here as FIG. 6A. This method is described more fully below.

There are two stages in the process; droplet formation, and the coalescence of droplets to form the hydrogel, as shown in FIG. 6A. For droplet formation, firstly a droplet of sodium alginate solution containing cells is formed from a nozzle located upstream of the microchannel using by introducing an aqueous phase into oil in a microchannel. The alginate droplet flows downstream in the main channel, following the flow of the continuous liquid phase. Secondly, the alginate droplet is fused with droplets of calcium chloride solution formed from a second nozzle located downstream.

In order to produce hydrogel beads smaller than 300 µm in their diameter, the channel depth is preferably about 50 µm, with a preferred diameter of 50 µm for the nozzle and 200 µm for the main channel, respectively.

Sodium alginate solution is preferably employed at a concentration of 1.5% by weight, and cells dispersed in the alginate at a concentration of $10^5$ cells/ml. Calcium chloride is preferably provided at a concentration of 0.1M. Vegetable oil such as sunflower oil can be used as the oil phase.

A second protocol has been described by Workman, et al., Macromolecular Rapid Communications, 2008, 29, 165). In this method, a shielded junction is employed to generate alginate microspheres (see FIG. 1 in Workman et al). Aqueous sodium alginate mixed with CaCO3 and cells is introduced into a central channel. Sunflower oil mixed with acetic acid is supplied to the outermost channels (A). Sunflower oil is supplied to the intermediate channels (B) to act as a shield preventing the alginate solution from coming into contact with the acidified oil flow. Between channels B and A the two oils flow in a laminar fashion, with minimal diffusion of H+ into the protective sunflower oil. After droplet formation at the junction, H+ diffuses into the alginate droplet, thus liberating $Ca^{2+}$ from CaCO3, which causes gelation of the alginate. Channels prior to the junction preferably have a cross-sectional area of about 500 µm$^2$, after the junction channels preferably about 1000 µm$^2$.

Encapsulation can moreover be performed using a jetting encapsulation technique. Many such techniques are known in the art; preferred are bio-electrospray jetting, aerodynamically-assisted bio jetting and pressure-assisted cell jetting.

Electrospraying is also known as bio-electrospraying or electrohydrodynamic jetting, and relies on a potential difference between a spray nozzle or needle and a grounded electrode to produce droplets of defined size.

The media are passed through a conducting needle that is held at a higher potential than the electrode, setting up an external electric field into which the media exiting the needle are passed. Needles are hollow, having an internal diameter of between 0.2 and 2 mm, and either flat or chamfered edge geometries. Needles may also be coaxial, such that different fluids can be sprayed from the same needle contemporaneously. The formation of the droplets is determined by the potential difference (difference in voltage) between the needle and the electrode, the flow rate of the medium and its relative features such as viscosity, surface tension, electrical conductivity and relative permittivity. Voltage and distance are related as the electric field depends on both variables. Normally, encapsulations are done at 1 or 2 cm distance with voltages around 5-10 kV. When the jet is stable, near monodistributions of droplet sizes can be achieved. Living cells can be encapsulated using this technology (Jayasinghe et al., (2006) Small 2, 216-219; and (2006) Biotechnol. J. 1:86-94). Although early experiments resulted in unstable jets with a wide dispersion of droplet sizes, this was improved using a coaxial jetting needle to create stable jetting (Jayasinghe et al., (2006) Lab Chip 6:1086-1090) with the microencapsulation material sprayed in the outer jet and the biomaterial in the inner jet.

Aerodynamically assisted jetting relies on a pressure gradient. A pressure is created in a chamber, with respect to the surrounding atmosphere, which provides the drawing effect to create the jet. Living cells can be encapsulated in this way (Arumuganathar et al., (2007) Biomed. Mat 2:158-168).

Pressure-assisted jetting employs a coaxial needle, where one orifice is used to jet the medium, and the second serves as the conduit for a pressure to be applied. Unlike aerodynamically-assisted jetting, there is no pressurised chamber.

For a general review of jetting technologies, see Jayasinghe, S., (2008) Regen. Med. 3:49-61, as well as U.S. Pat. No. 6,649,384, US 2006/0051329 and U.S. Pat. No. 4,353,888.

Jetting technologies can be scaled up by using multiple nozzles.

The cells to be encapsulated may be naked individual cells, or may be incorporated into microcarriers, such as spheres or porous microcarriers.

In one embodiment, in order to prepare the cell cores for encapsulation, the cell cores, which can be individual cells, are washed in a suitable aqueous buffer such as PBS, precipitated and resuspended in a buffer which may comprise the encapsulating polymer.

Encapsulation materials can be any suitable polymeric materials. The original encapsulation techniques used polydimethylsiloxane as the encapsulating material. Preferred are hydrogels, especially alginate. The polymer should be capable of ready solidification to form a membrane having the desired properties, and be insoluble in water or saline at physiological pH. The desired properties include nutrient permeability in vivo, and typically require that the polymer have a degree of polarity. The polymer membrane can typically contain 20-90% water at equilibrium. The polymer should be non-toxic to cells in solution. Examples of suitable polymers include polyacrylates and copolymers with acrylic acid, methacrylic acid and esters thereof, cellulose based polymers, copolymers containing acrylamides, N-vinyl pyrrolidone, styrene sulphonate, vinyl pyridine, vinyl alcohol, allyl alcohol and the like. A suitable polymer is a copolymer of acrylic acid ester and methacrylic acid ester, with small amounts of quaternary ammonium groups. See also U.S. Pat. No. 6,281,241; and Desai, 2002 Exp. Opin. Biol. Ther. 2:633-646. Generally, polymers useful for encapsulating cells for immuno-protection purposes, as known in the art, are useful in the present invention. For example, see Orive et al., (2003) Nature Medicine 9:104-107 and references cited therein.

The encapsulating polymer is preferably a PBS buffer lacking calcium ions and magnesium ions (this prevents premature solidification of the encapsulating polymer). Typically, the buffer may comprise 1-5% by weight of Alginate. Approximately 20 ml of a 3% alginate solution in PBS is required to encapsulate 1 g of microcarrier-based cell cores.

Labels or tags may be added to the encapsulating polymer solution, or to the cell cores before or after precipitation from PBS.

Gelling agents for the polymers can be introduced in one of three manners: (1) a secondary droplet population is generated and induced to fuse with the cell capsules; (2) the cell droplets are extracted into a water phase stream containing the polymerization agent established parallel to the oil phase; or (3) gelling agents are dissolved directly into the oil phase.

Preferably, $Ca^{2+}$, $Sr^{2+}$ or $Ba^{2+}$ ions are used to solidify the alginate. $CaCl_2$, or the respective Sr or Ba compounds, are dissolved in water at a concentration of between 10 mM and 1M. Combinations of Ca, Sr and Ba can be used with as little as 1 mM of one ingredient to achieve optimum bead properties. This solution is preferably held in a collection vessel, which is placed at the electrode of an electrospray unit. The cell cores, suspended in alginate solution, are passed through the spraying machine such that droplets are collected in the vessel which holds the solidifying or gelling solution. Encapsulated beads can be retrieved from the bottom of the vessel after spraying.

For re-encapsulation, the cell cores are already encapsulated at the start of the procedure. The encapsulated cell cores are advantageously washed in PBS and precipitated. 5 ml of an alginate solution prepared as above, preferably at a concentration of about 2% by weight, is used for every 1 ml volume of cell cores with the liquid removed, as above. A label or tag may also be added. The cores are jetted into a vessel containing a gelling agent, and re-encapsulated cores collected at the bottom of the vessel. Advantageously, a slightly larger needle diameter is used, for instance 0.9 mm, to compensate for the increased size of the biomaterial. In some embodiments, a higher flow rate and lower field strength can be used than in the primary encapsulation procedure.

In an alternative configuration, a coaxial spray needle can be used, with a cell suspension jetted in the inner needle and the encapsulating polymer solution in the outer needle. This arrangement has been shown to be capable of achieving a more stable jetting to encapsulate living cells (Jayasinghe & Townsend-Nicholson, (2006) Lab Chip 6:1086-1090).

Once the encapsulated stem cell core has been obtained, it can then be induced to differentiate. Induction of differentiation can be achieved by exposing the encapsulated stem cells to a particular culture condition. A culture condition may have multiple components to it. One such component may be a differentiation agent. The differentiation agent may be a molecular compound or a protein, for example. The permeability of the hydrogel capsules allow the agent to diffuse in and interact with the stem cells. The agent may, for example, interact with receptors on the surface of the cells, or within the cells in the cytoplasm or within organelles. The interaction may be stimulatory or inhibitory, but its effect is to direct the stem cell to produce differentiated cells. In other words, the differentiation agent promotes the differentiation of cells away from the stem cell phenotype towards another cell type.

In embodiments, the extent and efficiency of differentiation can be increased by exposing the encapsulated stem cell core to more than one culture condition, each culture condition being different from another. For example, each culture condition may contain a different differentiation agent, in place of or in combination with other differentiation agents, or a different concentration of the same differentiation agent. Without wishing to be bound by theory, it is believed that different culture conditions direct different stages of differentiation, therefore multiple consecutive culture conditions are required to direct a cell from a totipotent, pluripotent, multipotent, or primitive stage to a desired definitive, mature, or terminally differentiated stage.

Thus the invention also encompasses a method for obtaining differentiated cells from hydrogel encapsulated stem cells wherein the hydrogel encapsulated stem cells are progressively exposed to a first culture condition, followed by a second culture condition, and optionally followed by subsequent further culture conditions.

It may also be beneficial to culture the encapsulated stem cells for a period of time before directing them to produce differentiated cells, i.e. in the absence of a differentiation agent. In fact, any culture condition in the sequence may be free of differentiation agents. However, at least one culture condition in the sequence must promote differentiation and in the majority of cases multiple if not all culture conditions in the sequence are constituted to promote differentiation.

As mentioned in the summary section above, the identities or compositions of the culture conditions and the order or sequence in which the encapsulated stem cells are exposed to them form the differentiation protocols of the invention. In the examples, differentiation protocols for obtaining megakaryocytes, erythrocytes, and monocytes/macrophages are presented. However, differentiation protocols for other hematopoietic cells are also envisaged. In particular, existing protocols for the production of hematopoietic cells in culture other than in hydrogel capsules may be applied equally in the present invention, such as the protocols disclosed in Woll et al. 2009, Knorr et al. 2013, Ni et al. 2011, and Olivier et al. 2016. The attendant advantages of the invention (no EB, no ECM, no feeder cells, scalability, 3D culture) can thus also be obtained for all hematopoietic stem cells. Further improvements and refinements to these protocols can be achieved by the Combicult methods described and referenced herein. The Combicult methods can also be used to derive entirely new protocols for any of the production of any of the hematopoietic lineage cells. The methods of the invention may therefore be applied equally to the manufacture of hematopoietic lineage cells other than erythrocytes, macrophages, and platelets, including (but not limited to) hemogenic precursor cells, hemangioblasts, hemogenic endothelium cells, multipotent hematopoietic stem cells, multipotent hematopoietic progenitor cells, common myeloid progenitors, megakaryoblasts, promegakaryocytes, proerythroblasts, basophilic erythroblasts, polychromatic erythroblasts, orthochromatic erythroblasts (normoblasts), polychromatic erythrocytes (reticulocytes), mast cells, myeloblasts, B. promyelocytes, B. myelocytes, B. metamyelocytes, B. band cells, basophils, N. promyelocytes, N. myelocytes, N. metamyelocytes, N. band cells, neutrophils, E. promyelocytes, E. myelocytes, E. metamyelocytes, E. band cells, eosinophils, monoblasts, promonocytes, monocytes, myeloid dendritic cells, common lymphoid progenitors, lymphoblasts, prolymphocytes, small lymphocytes, B lymphocytes (B cells), plasma cells, T lymphocytes (T cells) including helper T cells (CD4+) and killer T cells (CD8+), natural killer cells (NK cells), and lymphoid dendritic cells.

In a preferred embodiment, the hematopoietic lineage cell manufactured by the method of the invention is a common myeloid precursor cell.

In a preferred embodiment, the hematopoietic lineage cell manufactured by the method of the invention is a common lymphoid precursor cell.

In a preferred embodiment, the hematopoietic lineage cell manufactured by the method of the invention is a natural killer cell.

In a preferred embodiment, the hematopoietic lineage cell manufactured by the method of the invention is a T lymphocyte.

In a preferred embodiment, the hematopoietic lineage cell manufactured by the method of the invention is a B lymphocyte.

The hydrogel encapsulated stem cells are exposed to each culture condition for at least a length of time necessary for the culture condition to have its effect. Its effect will be an observed change in the capsules, such as the observed phenotype of differentiating cells, the rate of production, the quantity of cells at each stage of differentiation, aggregate size, or any other observable characteristic indicative of a change. In embodiments, the length of time for a culture condition will be a matter of minutes or hours, such as from 1 minute to 1 hour, or from 1 hour to 6, 12, or 24 hours. In some cases, the length of time for a culture condition may be a matter of days or weeks, such as from 1 day, to 2, 3, 4, 5, or 6 days or more. The encapsulated stem cells may be contacted with each culture condition in a protocol for different lengths of time. For example, the initial culture condition may be used for from 1 to 4 days, the first different culture condition from 1 to 3 days, and a subsequent culture condition for 1 to 7 days. The exact pattern of exposure to culture conditions will be determined by the particular protocol being followed. An example protocol might involve exposing the encapsulated stem cells to the initial culture condition on days 1-4, the first different culture condition on days 5-7, and the second different culture condition from days 8-14.

For the production of hematopoietic cells from the encapsulated stem cells of the invention, the hydrogel capsules must be exposed to BMP4, VEGF and bFGF at the first and second stages of differentiation and then to:

TPO, SCF and one or more of IL3, IL6 and IL9 for megakaryocytes and platelets;

EPO, SCF and one or more of IL3, IL6 and FLT3 for erythrocytes; or

M-CSF, SCF and one or more of IL3, IL6 and GM-CSF for macrophages.

Suitable hematopoietic expansion media that can be used in the methods and protocols of the invention include, but are not limited to StemSpan ACF media (Stem Cell Technologies), StemPro34 serum-free medium (Invitrogen), Stemline II (Thermo Fisher), HPC Expansion Medium DXF (PromoCell), QBSF-60 (Quality Biological), StemMACS HSC expansion media XF (Miltenyi Biotec). In a preferred embodiment of the present invention the cells are cultured in StemSpan SFEM (Stem Cell Technologies). Any of the hematopoietic expansion media disclosed herein may replace SFEM, STEMLINE, or STEMLINE II in the culture, differentiation, and expansion of hematopoietic lineage cells in the protocols of the invention.

The present invention is scalable in a way that prior art methods of hematopoietic cell generation are not. It is reiterated that existing methods are struggling to meet the growing demand for hematopoietic cells from laboratories, hospitals, and everywhere in-between.

One of the limitations in the art is that stem cells are cultured in 2D as monolayers. In contrast, the present invention involves 3D culture of stem cells. Moreover, as each stem cell core is individually packaged in a protective hydrogel capsule, the culturing system of the invention lends its self to being scaled volumetrically. Thus, in a culture vessel of the invention, the entire volume may be occupied and made use of by the hydrogel encapsulated stem cells. In other words, the production capacity of a culture vessel according to the invention scales to the power of 3 (i.e. $x^3$) rather than to the power of 2 (i.e. $x^2$).

Another limitation which prevents existing stem cell culturing systems from being implemented on an industrial scale is a dependence on expensive support materials. For example, prior art culturing systems rely on stromal feeder layers, ROCK inhibitor, or extracellular matrix such as human collagen. The cost of these reagents is a barrier to significant hematopoietic cell production. The invention overcomes these limitations by eliminating reliance on these support materials, at least during the differentiation phase.

A further advantage of the invention which promotes scaling is that it circumvents the complex and often laborious process of embryoid body formation. Instead, the stem cells of the present invention may be obtained directly from passaging, or the more easily obtainable cell spheroids. The 3D environment inside the hydrogel capsule then provides the necessary support to ensure survival and propagation of the stem cell core.

The invention and its benefits will now be discussed in more detail with reference to the following specific examples.

Materials and Methods for the Examples

1. Feeder-Dependent Pluripotent Stem Cell Culture

SHEF1 hES cells (UK Stem Cell Bank) and SBI hiPS cells (Cambridge Bioscience) were grown on mitomycin C inactivated mouse embryonic fibroblasts in KO-DMEM (Life Technologies), 1× GlutaMAX (Life Technologies), 1×NEAA (Life Technologies), 0.1 mM β-mercaptoethanol (Sigma) and 4 ng/mL bFGF (R&D Systems). Cells were routinely passaged mechanically as small clumps following incubation in 0.7 mg/mL Collagenase IV (Life Technologies) for 4 min at 37° C.

2. Feeder-Free Pluripotent Stem Cell Culture

Feeder-free episomal hiPS cells (Invitrogen) were grown on 5 μg/mL vitronectin-coated plastic dishes in Essential 8 medium (Life Technologies). Cells were routinely passaged mechanically as small clumps.

3. Alginate Encapsulation

Alginate beads containing cell clumps were generated using an electrostatically-driven microencapsulator (Nisco). Briefly, mechanically harvested cell clumps were resuspended in a 2.0% (w/v) solution of sodium alginate in PBS (FMC, Philadelphia, USA). The alginate-cell suspension was dispensed through the 0.5 mm needle at a rate of 5 mL/h and a voltage of 7.7 kV. The droplets generated by this procedure were crosslinked into alginate beads by means of ionotropic gelling in a 200 mM calcium chloride solution. The size of alginate beads ranged between 300 and 400 uM. The resulting alginate beads were washed twice in DMEM (Life Technologies) before being resuspended in differentiation media and placed in an incubator at 37° C. with a humidified atmosphere of 5% CO2.

4. Differentiation of Pluripotent Cells into Megakaryocytes, Erythrocytes or Macrophages in Alginate Beads On d1 of the experiment, mechanically harvested clumps of iPS cells were encapsulated in alginate as described before and resuspended in the first differentiation media for each protocol. At each stage of differentiation (d4, d7 and d11) medium was decanted, beads washed twice in DMEM and the next medium in the series were added. For each protocol, two independent wells were prepared. On d14, cells released from alginate beads were stained with appropriate fluorophore labelled antibodies and analysed by FACS (flow cytometry). Cells inside of the beads were immunostained with the corresponding primary and secondary antibodies and analysed using a large particle flow sorter (Copas).

5. Immunostaining and FACS Analysis

Single cells were separated from large alginate beads and extruded aggregates by filtration through a 100 μm filter. Prior to staining with a specific antibody or the corresponding isotype control, cells were incubated in PBS supplemented with 3% FCS. Antibodies used were as follows: anti-human CD45-APC, anti-human CD41-PE, anti-human CD41-APC, anti-human CD42-APC anti-human CD62P-APC, anti-human CD235-PE, anti-human CD14-PerCP, anti-human HLA-DR-APC, anti-human CD206-PerCP (all purchased from BD Biosciences) and anti-human PF4-PE (R&D). Their corresponding isotype controls were anti-human IgG1-APC, anti-human IgG1-PE and anti-human IgG2-PE. Non-viable cells were gated out using staining with propidium iodide. Staining with corresponding isotype controls were used to define gating strategy. CountBright beads (Life Technologies) were used to assess absolute number of cells in the sample. Prior to staining with anti-PF4 antibody, cells were fixed with 2% PFA and permeabilized with 0.25% Triton X100. A FACS Canto II flow cytometer was used for analysis.

6. Immunostaining for Megakaryocytes in Alginate Beads

Cells encapsulated in alginate were washed in DPBS ($Mg^+Ca^+$) twice and fixed in 4% paraformaldehyde in DPBS for 30 min at room temperature. Following another two washes in DPBS ($Mg^+Ca^+$), cells were incubated in blocking solution (1% BSA in DPBS) for 1 h at 25° C. Cells were then incubated in the appropriate primary antibody diluted in blocking solution at 4° C. overnight. Following primary antibody incubation, beads were washed 4 times in DPBS (Mg$^+$Ca$^+$), further blocked for 1 h in blocking solution and incubated in secondary antibody solution at 4° C. overnight. Finally cells were washed 2 times in DPBS (Mg$^+$Ca$^+$) and resuspended in DPBS (Mg+ Ca+).

Antibodies used were as follows: primary: Ms anti-CD41a (BD), Rb anti-CD42b (Spring Bioscience), Rb anti-PF4 (Millipore) Secondary: Alexa Fluor 488 goat anti-mouse IgG, Alexa Fluor 488 goat anti-rabbit IgG, Alexa Fluor 594 goat anti-rabbit IgG (Life Technologies).

7. Beads Analysis

Beads were analysed using a COPAS PLUS (Union Biometrica) large particle flow sorter equipped with 488 nm and 561 solid state lasers and Green PMT 514/23 nm, Yellow PMT 585/20 nm, Red PMT 615/45 nm optical emission filters. The instrument was calibrated using a reference sample of beads. Sorting gates for size (TOF), optical density (EXT) and fluorescence parameters for each experiment were set using representative samples of beads that were labelled with secondary antibodies only.

8. Differentiation Protocols for Megakaryocyte in Suspension

On d0 of the experiment, feeder-free ehiPS cells were enzymatically harvested using Accutase (Sigma) (3 min incubation at 37° C.) and seeded on tissue culture plates coated with 5 µg/cm$^2$ collagen IV (Sigma) in Essential 8 media with 5 mM rock inhibitor. Media was changed to the first differentiation media for each protocol at d1. Media was then changed at the same time intervals as before (d4, d7 and d11). For the Lanza protocol, the media compositions were as previously reported (Feng et al, 2014). For each protocol, two independent wells were prepared. On d14, duplicate samples for each protocol were immunostained and analysed by FACS as described above.

9. FACS Analysis of Platelets

Prior to collection of platelets, 10 nM PGE and 0.5 u/ml apyrase were added to the culture media. Medium decanted from plates was centrifuged at 300×g for four minutes to separate platelets in suspension from the cell sediment. All further centrifugations of the platelet fraction were conducted at 1000×g for ten minutes. Prior to staining with a specific antibody or the corresponding isotype control, cells were incubated in PBS supplemented with 3% FCS (fetal calf serum). Antibodies and corresponding isotype controls used were as follows: anti-human CD41-PE, anti-human CD42-APC, anti-human IgG-APC and anti-human IgG-PE (all purchased from BD Biosciences). A FACS Canto II flow cytometer was used for analysis.

10. Platelet Functional Assays

Prior to analysis using functional assays, platelets were washed once with Tyrode buffer, then incubated with one of the following activators: 5 uM ADP, 1 u/ml Thrombin, 0.5 uM collagen or 0.5 mM TRAP peptide for 5 min. Platelets were then incubated with CD62p antibodies (BD) or appropriate isotype control for 10 min followed by quick fixation in 1% PFA. Samples were washed in PBS supplemented with 3% FCS and analysed by FACS.

For the fibrinogen binding assay, slides were pre-incubated overnight at 4° C. either with fibrinogen solution (100 ug/ml) or with BSA solution (5 mg/ml). Slides were then washed with PBS and incubated with washed platelets for 90 min at 37° C. Following incubation slides were washed to remove unbound platelets, fixed with 2% PFA and stained with both phalloidin 488 and anti-PF4 primary antibody. This was followed by incubation with anti-mouse Alexa Fluor 594 secondary antibody and Hoechst. Platelet spreading on fibrinogen was analysed using a Nikon Eclipse 2000-S inverted epifluorescent microscope equipped with filter sets for visualization of TRITC, DAPI, GFP-B (all from Nikon) and Cy5.5 (Chroma Technology). Platelets were defined by a positive signal for PF4 (shown red in images), whilst activated platelets were defined as those that appeared as large, spread bodies with long actin stress fibres (shown green in images). Unactivated platelets were defined as those appearing as smaller, rounded bodies.

11. Phagocytosis Assay

Cells were washed in DPBS and incubated with 1 mg/mL pHrodo *E. coli* BioParticles conjugate (Molecular Probes) in HBSS/HEPES buffer (pH 7.4) at 37° C. for 2 hrs. The supernatant was removed, cells were washed with HBSS/HEPES buffer (pH 7.4), incubated in Hoechst solution (1 ug/ml) at 37° C. for 20 min, washed with HBSS/HEPES buffer (pH 7.4) and photographed using a Nikon Eclipse 2000 microscope.

12. qPCR of Megakaryocytes

At day 0 of the MK differentiation, undifferentiated iPS cells were collected by 300×g centrifugation for four minutes. Cell pellets were washed with PBS, dehydrated and frozen at −80° C. At day 4 to release cells from alginate beads the beads were dissolved by incubation in Trypsin/EDTA for 30 mins at 37° C. At day 7, cells extruded from the alginate were picked out manually using a pipette under a microscope. These cells were collected by centrifugation as described earlier. Finally at day 14, single MK cells were filtered through a 70 µm membrane and collected by centrifugation.

RNA was first extracted from cell pellets using the RNeasy Micro Kit (Qiagen, Germany) according to the manufacturer's instructions. The RNA was eluted in 40 µL of RNase-free water and the concentration was measured using a Nanodrop spectrophotometer (Thermo Scientific, Delaware, USA), measuring absorbance at wavelengths of 260 nm and 280 nm. 1 ug of RNA was used to synthesise first strand cDNA using the QuantiTect Reverse Transcription kit (Qiagen, Germany), as per the manufacturer's instructions.

For gene expression analysis 1 µL of the cDNA was used in a SYBRGreen real time PCR reaction using the SsoAdvanced Universal SYBR Green Supermix (Biorad, Hercules, USA) and the pre-validated QuantiTect Primer Assays (Qiagen, Germany) under the manufacturer's protocols, in a CFX Connect Real-Time PCR detection system (Bio-Rad, Hercules, USA). Primer sequences are proprietary but details can be found at qiagen.com/GeneGlobe/Default.aspx. Primer assays for hemangioblasts were as follows: Gata1 (QT00000420) and Tal1 (QT00012530); whilst primer assays for megakaryocyte differentiation were as follows: Mpl (QT00014511), Znf385 (QT00070315), Nf-e2 (QT00203329) and Myh9 (QT00073101). For relative quantification, the DDCt method (Pfaffl, 2001) was used. RNA levels were normalised against the housekeeping gene GAPDH. Expression was quantified as a fold-increase or decrease normalised against undifferentiated cells. All calculations were performed using the CFX manager software (Bio-Rad, Hercules, USA).

13. Differentiation in the WAVE Bioreactor

A 2 L WAVE bag was used for scale up the production of megakaryocytes. The inflated bag was filled with 300 ml of Stemline medium (Sigma Aldrich) and left rocking at 2 rpm@6° for 2 hours in order to equilibrate the pH and dissolved oxygen sensors on the WAVE bioreactor (GE). After 2 hours, 100 mL of Stemline media containing BMP4 (250 ng/ml), VEGF (250 ng/ml) and bFGF (250 ng/ml) was added to the WAVE bag using the WAVE system's peristaltic feeding line. Alginate beads containing ehIPS cells were suspended in 100 mL of Stemline medium before being inoculated with a 100 mL Luer-fitted syringe (BD) through the Luer sampling port on the WAVE bag. Rocking settings were as follows: 2 rpm@6°. To change media, 250 mL of spent media was firstly removed using the peristaltic harvesting line on the WAVE system (flowrate: 25 L/day). 250 mL of DMEM (Invitrogen) was then added using the peristaltic feed line followed by removal of 250 mL of liquid from the bag using the peristaltic harvesting line. This process was repeated with the appropriate basal media for the next stage (Stemline at day 4, SFEM at days 7 and 11). Finally, 250 mL of media for the next stage of differentiation was added (supplemented with 2× concentration of cytokines, growth factors and small molecules as listed for protocol #5 in Table 1). Harvesting was performed in a laminar flow cabinet by opening the harvest line and allowing contents of the bag to flow out by means of gravity into a container. Harvested material was treated as before to prepare for analysis.

14. Generation of Embryoid Bodies Using Spheroidal Culture Method

Feeder-free eh-IPS cells were harvested from the plates by incubating in 0.1 mL/cm2 of 0.2% Versene EDTA (Lonza, Basal, Switzerland) for 20 mins. Following quenching in basal media and subsequent centrifugation, cells were resuspended in DEF-CS 500 Xeno-Free Basal Media supplemented with DEF-CS Xeno-Free 3D Spheroid Additives (Takara Bio USA, Mountain View, USA). Resuspended cells were transferred to tissue culture flasks and placed on an orbital shaker (speed of 70 rpm) inside a humidified cell culture incubator (5% CO2; 37° C. temperature). 24 hrs later, spheroids were encapsulated in alginate and differentiated as previously described.

15. Media Components (i) DMEM

| DMEM | Conc (mg/ml) |
|---|---|
| Glycine | 30 |
| L-Alanyl-L-Glutamine | 862 |
| L-Arginine hydrochloride | 84 |
| L-Cystine 2HCl | 63 |
| L-Histidine hydrochloride-$H_2O$ | 42 |
| L-Isoleucine | 105 |
| L-Leucine | 105 |
| L-Lysine hydrochloride | 146 |
| L-Methionine | 30 |
| L-Phenylalanine | 66 |
| L-Serine | 42 |
| L-Threonine | 95 |
| L-Tryptophan | 16 |
| L-Tyrosine | 72 |
| L-Valine | 94 |
| Choline chloride | 4 |
| D-Calcium pantothenate | 4 |
| Folic Acid | 4 |
| Niacinamide | 4 |
| Pyridoxine hydrochloride | 4 |
| Riboflavin | 0.4 |
| Thiamine hydrochloride | 4 |
| i-Inositol | 7.2 |
| Calcium Chloride ($CaCl_2$—$2H_2O$) | 264 |
| Ferric Nitrate ($Fe(NO_3)_3$·$9H_2O$) | 0.1 |
| Magnesium Sulfate ($MgSO_4$—$7H_2O$) | 200 |
| Potassium Chloride (KCl) | 400 |
| Sodium Bicarbonate ($NaHCO_3$) | 3700 |
| Sodium Chloride (NaCl) | 6400 |
| Sodium Phosphate monobasic ($NaH_2PO_4$—$2H_2O$) | 141 |
| D-Glucose (Dextrose) | 4500 |

-continued

| DMEM | Conc (mg/ml) |
|---|---|
| Phenol Red | 15 |
| Sodium Pyruvate | 110 |

(ii) Essential 8

| Essential 8 | Conc (mg/L) |
|---|---|
| DMEM/F12 | |
| L-ascorbic acid-2-phosphate magnesium | 64 |
| Sodium selenium | 0.014 |
| FGF2 | 0.1 |
| Insulin | 19.3 |
| $NaHCO_3$ | 543 |
| Transferrin | 10.7 |
| TGFB1 | 0.002 |
| NODAL | 0.1 |

(iii) HBSS

| HBSS | Conc (mg/ml) |
|---|---|
| $CaCl_2$—$H_2O$ | 0.185 |
| $MgSO_4$ | 0.09767 |
| KCl | 0.4 |
| $KH_2PO_4$ | 0.06 |
| $NaHCO_3$ | 0.35 |
| NaCl | 8 |
| $Na_2HPO_4$ | 0.04788 |
| D-Glucose | 1 |

(iv) Tyrode's Solution

| Tyrode's Solution | Conc (mg/ml) |
|---|---|
| $CaCl_2$—$H_2O$ | 0.265 |
| $MgCl_2$—$H_2O$ | 0.214 |
| KCl | 0.2 |
| $NaHCO_3$ | 1 |
| NaCl | 8 |
| $Na_2H_2PO_4$ | 0.05 |
| D-Glucose | 1 |

(v) DMEM/F12

| DMEM/F12 | Conc (mg/L) |
|---|---|
| Glycine | 18.75 |
| L-Alanine | 4.45 |
| L-Arginine hydrochloride | 147.5 |
| L-Asparagine-$H_2O$ | 7.5 |
| L-Aspartic acid | 6.65 |
| L-Cysteine hydrochloride-$H_2O$ | 17.56 |
| L-Cystine 2HCl | 31.29 |
| L-Glutamic Acid | 7.35 |
| L-Glutamine | 365 |
| L-Histidine hydrochloride-$H_2O$ | 31.48 |
| L-Isoleucine | 54.47 |
| L-Leucine | 59.05 |
| L-Lysine hydrochloride | 91.25 |
| L-Methionine | 17.24 |
| L-Phenylalanine | 35.48 |

-continued

| DMEM/F12 | Conc (mg/L) |
| --- | --- |
| L-Proline | 17.25 |
| L-Serine | 26.25 |
| L-Threonine | 53.45 |
| L-Tryptophan | 9.02 |
| L-Tyrosine disodium salt dihydrate | 55.79 |
| L-Valine | 52.85 |
| Biotin | 0.0035 |
| Choline chloride | 8.98 |
| D-Calcium pantothenate | 2.24 |
| Folic Acid | 2.65 |
| Niacinamide | 2.02 |
| Pyridoxine hydrochloride | 2.013 |
| Riboflavin | 0.219 |
| Thiamine hydrochloride | 2.17 |
| Vitamin B12 | 0.68 |
| i-Inositol | 12.6 |
| Calcium Chloride ($CaCl_2$) (anhyd.) | 116.6 |
| Cupric sulfate ($CuSO_4$—$5H_2O$) | 0.0013 |
| Ferric Nitrate ($Fe(NO_3)3"9H_2O$) | 0.05 |
| Ferric sulfate ($FeSO_4$—$7H_2O$) | 0.417 |
| Magnesium Chloride (anhydrous) | 28.64 |
| Magnesium Sulfate ($MgSO_4$) (anhyd.) | 48.84 |
| Potassium Chloride (KCl) | 311.8 |
| Sodium Bicarbonate ($NaHCO_3$) | 2438 |
| Sodium Chloride (NaCl) | 6995.5 |
| Sodium Phosphate dibasic ($Na_2HPO_4$) anhydrous | 71.02 |
| Sodium Phosphate monobasic ($NaH_2PO_4$—$H_2O$) | 62.5 |
| Zinc sulfate ($ZnSO_4$—$7H_2O$) | 0.432 |
| D-Glucose (Dextrose) | 3151 |
| Hypoxanthine Na | 2.39 |
| Linoleic Acid | 0.042 |
| Lipoic Acid | 0.105 |
| Phenol Red | 8.1 |
| Putrescine 2HCl | 0.081 |
| Sodium Pyruvate | 55 |
| Thymidine | 0.365 |

(vi) DPBS (1x)

| DPBS (1x) Ca, Mg | Conc (mg/mL) |
| --- | --- |
| $CaCl_2$ | 0.1 |
| $MgCl_2$—$6H_2O$ | 0.1 |
| KCl | 0.2 |
| $KH_2PO_4$ | 0.2 |
| NaCl | 8 |
| $Na_2HPO_4$—$7H_2O$ | 2.16 |

(vii) IMDM

| DPBS (1x) Ca, Mg | Conc (mg/mL) |
| --- | --- |
| $CaCl_2$ | 0.1 |
| $MgCl_2$—$6H_2O$ | 0.1 |
| KCl | 0.2 |
| $KH_2PO_4$ | 0.2 |
| NaCl | 8 |
| $Na_2HPO_4$—$7H_2O$ | 2.16 |

An alternative to Stemline II media published in US patent application publication number 2015/0313944 A1 may comprise: Iscove's modified Dulbecco's medium (IMDM), Ham's F-12 nutrient mixture, Albucult (rh Albumin), Polyvinylalcohol (PVA), Linoleic acid, SyntheChol (synthetic cholesterol), Monothioglycerol (α-MTG), rh Insulin-transferrin-selenium-ethanolamine solution, protein-free hybridoma mixture II (PFHMII), ascorbic acid 2 phosphate, Glutamax I (L-alanyl-L-glutamine).

In embodiments, Essential 8 medium can be used in place of KO-DMEM.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Survival and Differentiation of Pluripotent Cells in Alginate Beads Improved when Cells were Encapsulated as Small Clumps Rather than Single Cells Human hES cell line Shef1 and human iPS cell line SBi were passaged mechanically on MEF feeder layers. Prior to encapsulation cell colonies were either disrupted mechanically into small homogeneous clumps or harvested enzymatically with accutase solution to obtain a single cell suspension. Alginate beads containing cell clumps or single cells were generated using electro spraying technology. Following centrifugation resuspended pellets containing single cells or cell clumps were mixed with 2% alginate solution. Alginate droplets were dispensed through the nozzle of the microencapsulator (Nisco) using electro-static force and hardened into alginate beads by crosslinking in 200 mM calcium chloride. Alginate beads containing cell fragments were washed and placed into the first differentiation media for megakaryocyte differentiation (protocol #32), which may comprise STEMLINE (Sigma), BMP4 (50 ng/ml) and VEGF (50 ng/ml). Following 2 days of differentiation (Day 3) alginate beads with cells inside were transferred into media containing STEMLINE (Sigma), BMP4 (10 ng/ml), VEGF (10 ng/ml), FGF (10 ng/ml), Ascorbic Acid (50 ug/ml) and β-mercaptoethanol (0.1 mM). At Day 5 the media was replaced with the same media without β-mercaptoethanol. At Day 7 beads with cells inside were transferred into SFEM (Stemcell Technologies) supplemented with TPO (50 ng/ml), SCF (50 ng/ml), IL6 (20 ng/ml), IL9 (10 ng/ml) and LDL (10 ug/ml). Cell viability in alginate was monitored at each stage of differentiation by taking representative samples of beads and staining cells inside with Calcein AM (Life Technologies, 1 ug/ml). The efficiency of megakaryocyte differentiation was assessed at day 14 by immunocytochemistry staining for megakaryocyte-specific markers CD41a and CD42b. Applicants' results revealed that when hES and iPS cells were encapsulated as a single cell suspension they showed low viability, didn't proliferate and didn't differentiate into CD41a/CD42b positive megakaryocytes (FIG. 1A, B). Moreover treatment with Rock inhibitor (5 ug/ml) (which has been previously shown to reduce apoptosis and improve survival of pluripotent cells when they are split enzymatically and seeded as single cells), didn't improve the outcome of single cell hES/hiPS differentiation in alginate beads. However when hES and hiPS cells were harvested mechanically and encapsulated as small clumps, cells retained high viability at all stages of differentiation (FIG. 1A) and successfully differentiated into CD41a/CD42b positive megakaryocyte inside alginate beads (FIG. 1B).

Figure 2:
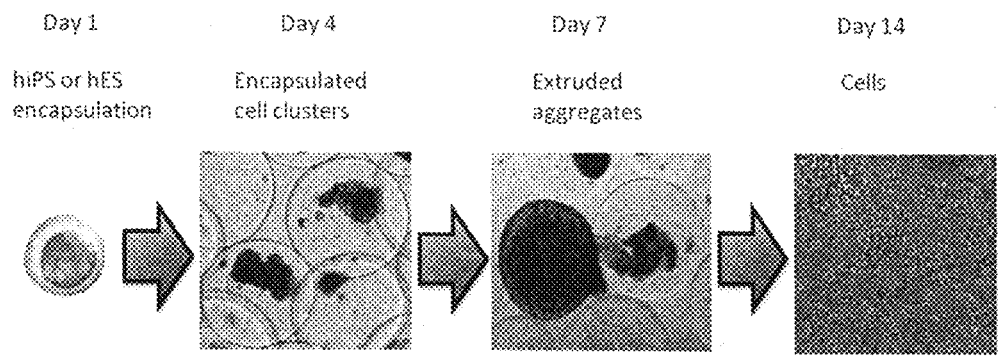
FIG. 2A-2F. Initiation of hematopoietic differentiation of hES and hiPS cells in 3D alginate scaffolds: A. Mechanically disrupted hiPS cells were encapsulated in alginate beads as cells clusters and underwent 4-stage hematopoietic differentiation. B. Immunostaining of colonies inside of alginate beads and cell aggregates extruded from beads at day 7 of hematopoietic differentiation revealed expression of surface markers specific for hemogenic endothelium. (i) List of studied markers and their role in hematopoiesis. (ii) Immunostaining of cells inside and outside of alginate beads: row 1—undifferentiated eh-iPS cells at Day 1; row 2 and 3: hemogenic precursor cells at Day 7 of hematopoietic differentiation according to protocol 21 (row 2) and protocol 5 (row 3). C. Expression of two genes (GATA1 and TAL1) associated with appearance of hemogenic endothelium was analysed by qPCR at three time-points. At day 0, RNA was extracted from undifferentiated iPS cells. At day 4, RNA was extracted from cells released from alginate beads. At day 7, RNA was extracted from cell aggregates extruded from alginate beads. Gene expression was normalised to the internal control gene GAPDH. Expression was measured in two cell lines, using two Combicult-derived protocols: (i) & (ii) SBi iPS; (iii) & (iv) eh-iPS; (i) & (iii) Protocol 5; (ii) & (iv) Protocol 21. D. Analysis of megakaryocyte differentiation by FACS. E. Analysis of erythrocyte differentiation by brightfield microscopy (i) and FACS (ii). F. Analysis of differentiation of eh-iPS cells into monocyte/macrophage lineage: (i) Flow cytometry analysis at Day 18 and Day 22 of differentiation; (ii) pHRodo phagocytosis assay (blue—Hoechst, red—pHrodo bioparticles); (iii) polarisation into M1 and M2 phagocytes.
Figure 2:
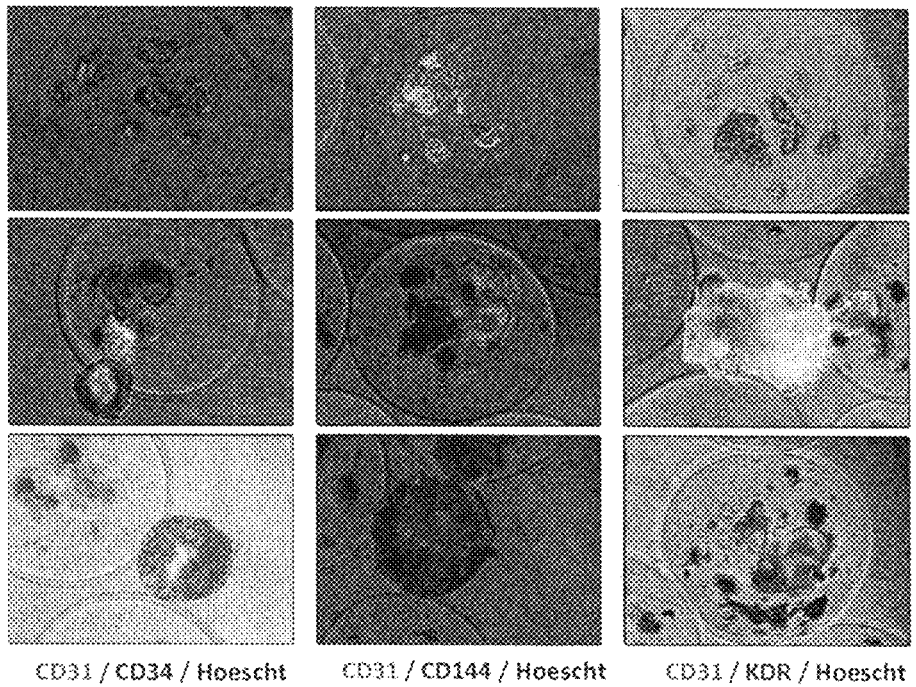
Figure 2:
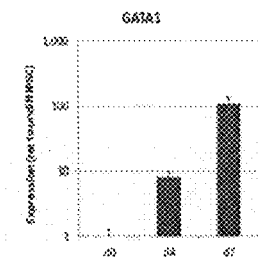
Figure 2:
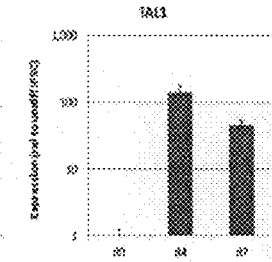
Figure 2:
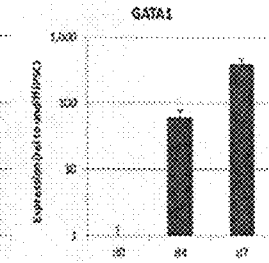
Figure 2:
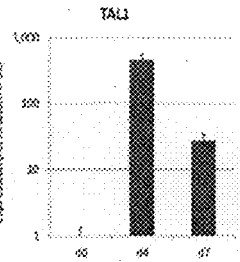
Figure 2:
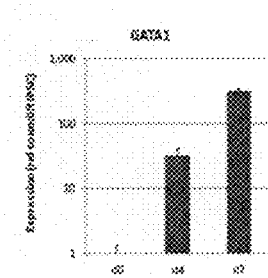
Figure 2:
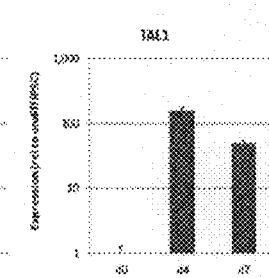
Figure 2:
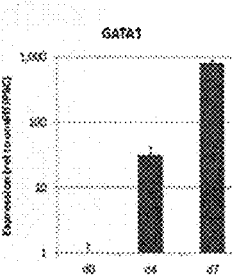
Figure 2:
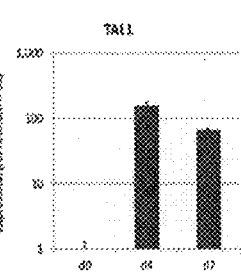
Figure 2:
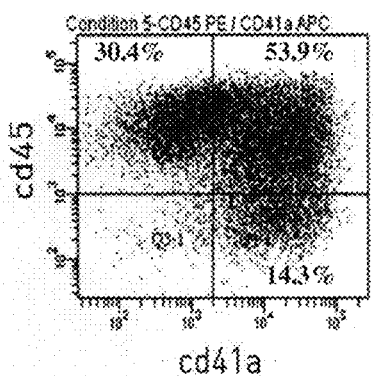
Figure 2:
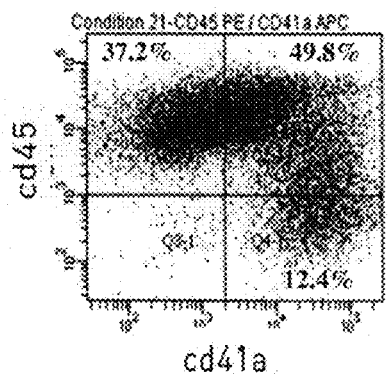
Figure 2:
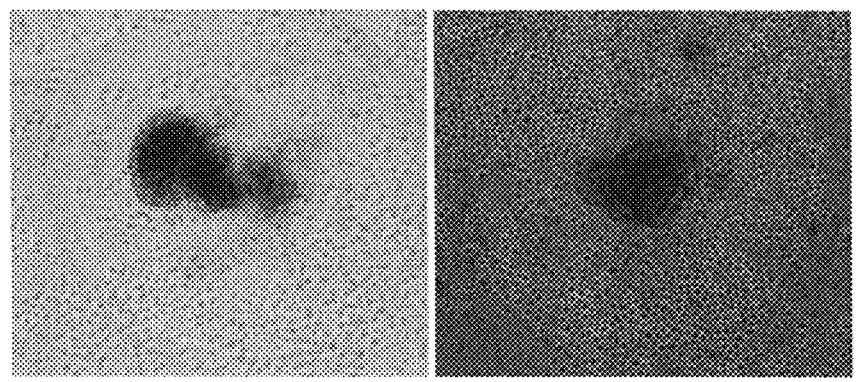
Figure 2:
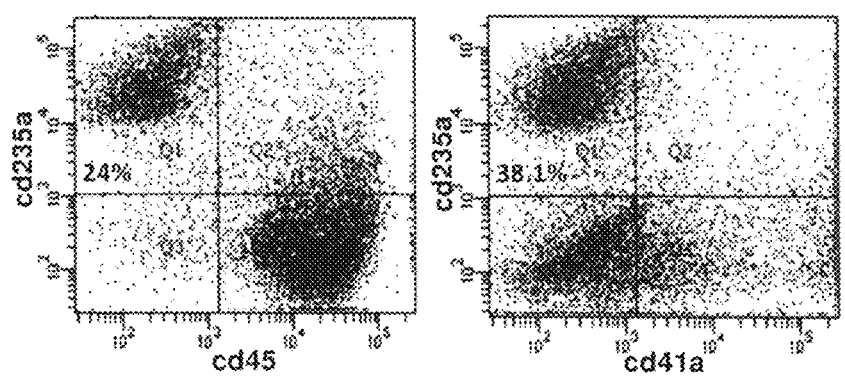
Figure 2:
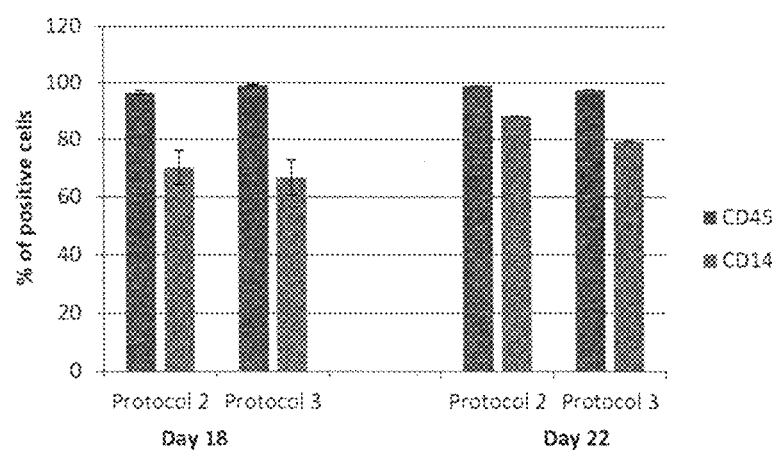
Figure 2:
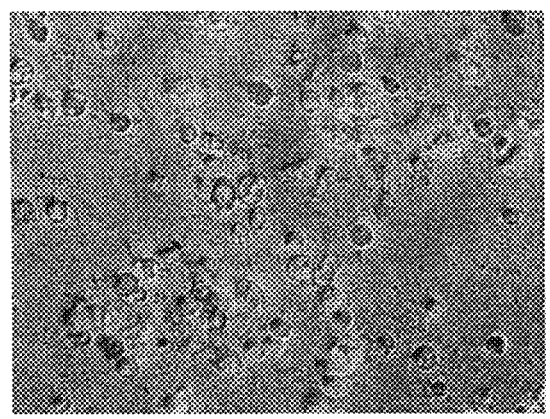
Figure 2:
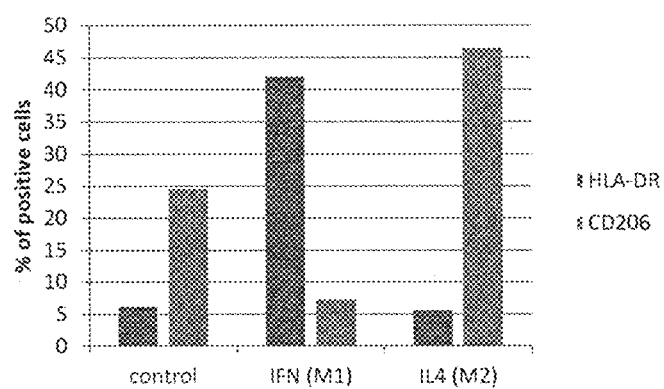

Example 2: Pluripotent Cells Encapsulated in Alginate Beads Differentiate into Hematopoietic Progenitors Human iPS cell lines SBi and eh-iPS as well as human hES cell line Shef1 were passaged mechanically as small clumps. Prior to encapsulation cell colonies were disrupted into small homogeneous clumps containing 100-150 cells and mixed with alginate solution. iPS-SBi cells that are routinely passaged on feeder cells did not require weaning off feeders prior to alginate encapsulation. Alginate beads containing cell clumps were generated using electro spraying technology. Alginate droplets were dispensed through the nozzle of the microencapsulator (Nisco) using electrostatic force and hardened into alginate beads by crosslinking in 200 mM calcium chloride. Alginate beads containing cell fragments were washed and placed into the first differentiation media that comprised of STEMLINE (Sigma), BMP4 (50 ng/ml), VEGF (50 ng/ml) and FGF2 (50 ng/ml). After 3 days of differentiation (Day 4) media was discarded and beads were placed into the second differentiation media which may comprise of STEMLINE (Sigma), BMP4 (10 ng/ml), VEGF (10 ng/ml), FGF2 (10 ng/ml), ascorbic acid (50 ug/ml) and β-mercaptoethanol (0.1 mM) (Protocol #5) or STEMLINE (Sigma), BMP4 (50 ng/ml), VEGF (50 ng/ml), FGF2 (20 ng/ml), SCF (20 ng/ml), TPO (20 ng/ml), Valproic acid (10 uM) (protocol #21) or Stemline (Sigma), VEGF (80 ng/ml), FGF2 (25 ng/ml), SCF (100 ng/ml) (monocyte/macrophage protocol). Beads containing cells were incubated in this media for 3 more days. At the second stage of differentiation, cells derived from both ehiPS and SBi iPS cell lines as well as from the hES Shef1 cell line underwent rapid proliferation and formed large compact colonies that extruded from the alginate beads by Day 7 (FIG. 2A). Small number of cell fragments didn't extrude and underwent further differentiation inside the beads. Extruded cell aggregates derived from ehiPS cell line were collected and fixed with 2% PFA in DPBS. Surface markers flk1 (also known as KDR or VEGFR2), CD144 (also known as VECadherin), CD31 (also known as PECAM) and CD34 that are specific for hemangioblasts and/or hemogenic endothelium cells were analysed by immunocytochemistry (ICC) (FIG. 2B (i)). Results revealed that at day 7 of differentiation most extruded aggregates contained CD31 positive cells (FIG. 2B (ii)). The level of expression of CD34, KDR and VE Cadherin in aggregates outside of the alginate beads was higher in cells differentiated according to protocol #21 compared to protocol #5. Small proportion of colonies inside the beads was positive for hemangioblast/hemogenic endothelium markers (FIG. 2B (ii)). Undifferentiated eh-iPS cells that were fixed straight after encapsulation stained negatively for all studied markers (FIG. 2B (ii)).

Expression of transcription factors GATA1 and TAL1 (also known as SCL1), which are both indicative of the early stages of hematopoietic differentiation (Elefanty et al, 1997, Zambidis et al, 2005, Kennedy et al, 2007) was analysed by qPCR in hematopoietic progenitors generated from ehiPS and SBi iPS cell lines. Cells were differentiated in alginate beads according to protocol #5 and #21 as described above. RNA was extracted from undifferentiated cells prior to encapsulation (Day 0), from cell aggregates inside of alginate beads at Day 4 of differentiation (beads were dissolved by treatment with trypsin/EDTA), and from cell aggregates extruded from alginate beads at Day 7 of differentiation. The qPCR data indicates that the level of expression of GATA1 progressively increases upon hematopoietic differentiation from Day 0 to Day 7 whilst level of Tal1(Scl1) expression peaks at day 4 before slightly dropping in the extruded aggregates at Day 7 (FIG. 2C (i) and (ii) for SBi iPS and (iii) and (vi) for ehiPS).

In order to explore the multipotent properties of hematopoietic progenitors initiated in alginate beads, both beads and extruded aggregates were further exposed to media compositions that are known to direct differentiation into megakaryocytic, erythrocytic and monocyte/macrophage lineages. For Megakaryocyte differentiation two recently developed protocols (protocol #5 and protocol #21) were used. For protocol #5, Day 7 beads and aggregates were incubated for 4 days in the media that comprised of SFEM, TPO (50 ng/ml), SCF (50 ng/ml), FLT3 (50 ng/ml), IL6 (20 ng/ml), IL9 (10 ng/ml), heparin (5 ug/ml) and valproic acid (10 uM). For protocol 21 Day 7 beads and aggregates were incubated for a further 4 days in the media which may comprise STEMLINE, SCF (20 ng/ml), Compound P (500 nM), GPR40 (100 nM), Metformin (2 mM) and Heparin (5 ug/ml). For both protocols on Day 11 beads, aggregates and cells fallen off aggregates were transferred to SFEM media supplemented with TPO (50 ng/ml), SCF (50 ng/ml), IL6 (10 ng/ml), IL9 (10 ng/ml), Nicotinomide (2.5 mM) and Arachoidoic acid (5 uM) and cultivated for further 3-4 days. On day 14-15 non-adherent suspension cells were collected using 100 uM sieve, immunostained and analysed by FACS. High levels of expression of pan-leucocyte marker CD45 and megakaryocyte marker CD41a in 60-80% of cells indicated successful differentiation of hematopoietic precursors into the megakaryocyte lineage (FIG. 2D).

For erythrocyte differentiation Day 7 beads containing cell clusters and free-floating cell aggregates were placed in SFEM media containing SCF (50 ng/ml), TPO (50 ng/ml), FLT3 (50 ng/ml), IL3 (10 ng/ml), IL6 (10 ng/ml) and EPO (3 u/ml). On Day 11 media was changed to SFEM supplemented with SCF (100 ng/ml), IL3 (5 ng/ml) and EPO (3 u/ml). After 3 days of incubation in this media (on day 14 of differentiation) non-adherent suspension cells were separated from beads and cell aggregates (FIG. 2E (i)), immunostained for erythrocyte-specific marker CD235a (Glycophorin A) and pan-leucocyte marker CD45 and subjected to flow cytometry analysis, revealing two distinct populations. 24% of cells were CD45 negative/CD235a positive, indicating the emergence of primitive erythropoiesis (FIG. 2E (ii)).

To differentiate cells into the monocyte/macrophage lineage, Day 4 beads containing cell clusters were incubated in the second stage differentiation media, which comprised of Stemline (Sigma), VEGF (80 ng/ml), FGF2 (25 ng/ml) and SCF (100 ng/ml) (Protocol 2) or STEMLINE (Sigma), BMP4 (10 ng/ml), VEGF (10 ng/ml), FGF2 (10 ng/ml), ascorbic acid (50 ug/ml) and β-mercaptoethanol (0.1 mM) (Protocol 3). On Day 7, beads and extruded cell aggregates were placed in SFEM media containing a mixture of cytokines previously described to promote monocyte/macrophage differentiation: SCF (50 ng/ml), FLT3 (50 ng/ml), IL3 (50 ng/ml), TPO (5 ng/ml) and M-CSF (50 ng/ml) (Protocol 2) or IL3 (25 ng/ml), M-CSF (50 ng/ml) (Protocol 3) (Yanagimachi et al, 2013, Lachmann et al, 2015). On Day 11, 15 and 18 media was changed/refreshed with SFEM supplemented with FLT3 (50 ng/ml), GM-CSF (25 ng/ml) and M-CSF (50 ng/ml) (Protocol 2) or IL3 (25 ng/ml), M-CSF (50 ng/ml) (Protocol 3). Flow cytometry analysis on Days 18 and Day 22 demonstrated that 97-99% of the cell population was comprised of CD45 positive hematopoietic cells and by Day 22 80-90% of the cell population consisted of CD14 positive monocytes/macrophages (FIG. 2 F (i)). Phagocytic activity of Day 22 monocytes/macrophages was confirmed using the pHrodo phagocytosis assay, which showed that 70-80% of cells actively engulfed *E. coli*-conjugated fluorescent micro-particles (FIG. 2 F (ii)). Applicants had also demonstrated that macrophages produced by this method can be polarized into two functionally distinct subtypes (M1 and M2) following induction with interferon-γ (IFN) and IL4, respectively (FIG. 2 F (iii)). 24 hr incubation in the presence of IFN (20 ng/ml) or IL4 (50 ng/ml) led to induction of surface markers that characterise primary M1 and M2 macrophages (HLA-DR and CD206 respectively).

Altogether, this example demonstrates a novel method for initiation of human pluripotent stem cells differentiation by means of encapsulation of undifferentiated cell clusters into alginate beads and culture in media that together induce fast and efficient differentiation into hematopoietic precursors which can be further differentiated into a range of hematopoietic lineages. Furthermore this method gives a selective advantage to the fraction of hematopoietic precursors that undergo a burst of proliferation during the progenitor stage in response to specific growth factors signalling and break free from alginate while undifferentiated cells stay inside the beads and can be easily removed. Importantly, this method allows pluripotent stem cell differentiation to be achieved at large scale and with cost efficiencies compatible with industrial production in suspension format bioreactor systems.

Example 3: Novel Scalable Protocols for Megakaryocyte Differentiation from Pluripotent Cells Using 3D Alginate Scaffolds Novel protocols that promote differentiation of pluripotent (hES and hiPS) cells into mature Megakaryocytes were discovered through the use of the second generation CombiCult screening platform in which differentiating cells are entrapped inside of alginate beads allowing detection of non-adherent cells. CombiCult technology allows to screen several iPS/ES cell lines simultaneously leading to the discovery of protocols that work efficiently across a range of cell lines. In these protocols, the first stages of differentiation from pluripotent stem cells into early hematopoietic progenitors take place inside of alginate beads thereby replacing the requirement for embryoid body formation, stromal feeder layers or expensive ECM. The size and number of encapsulated fragments per alginate bead defines whether differentiating cells stay inside of the beads through the course of differentiation. This allows for the detection of mature, non-adherent megakaryocytes at the end of experiment, leading to the unraveling of novel differentiation protocols. Encapsulation at higher density leads to fast and extensive cell proliferation that results in hemangioblasts being extruded from alginate beads, leaving behind cells that fail to differentiate thereby increasing homogeneity of progenitors and synchronizing cells for further differentiation.

Human iPS cell lines SBi and eh-iPS and human ES cell line Shef1 were passaged mechanically as small clumps. Prior to encapsulation cell colonies were disrupted into small homogeneous clumps containing 100-150 cells and mixed with alginate solution. Alginate beads containing cell clumps were generated using electro spraying technology. Alginate droplets were dispensed through the nozzle of the microencapsulator (Nisco) using electro-static force and hardened into alginate beads by crosslinking in 200 mM calcium chloride. Beads containing cell fragments were washed and placed into their corresponding differentiation media. At each stage of differentiation (d4, d7 and d11) media was decanted, beads were washed twice in DMEM and the next media in the series was added (Table 1). For each protocol validated, two independent wells were prepared. On d14, duplicate samples for each protocol were immunostained and analyzed by FACS. For iPS cell lines FACS analysis of non-adherent cells released from alginate beads at the end of differentiation protocol demonstrated that 70-90% of cells were blood cells (CD45 positive) and 50-60% were MKs (CD41a positive) (FIG. 3A (i) & (ii)). 50-60% of differentiated cells were positive for both CD41a and CD42b markers. For the hES cell line, 80-90% of cells population were CD41a positive megakaryocytes (FIG. 3A (iii)).

Figure 3:
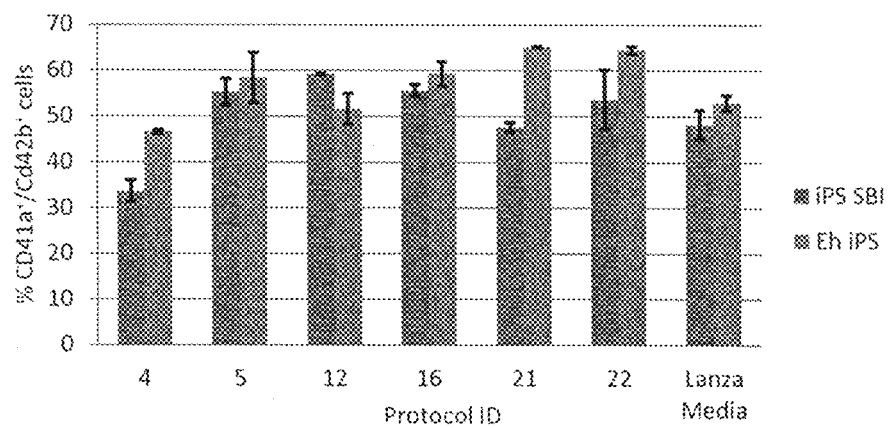
FIG. 3A-3E. Characterisation of Megakaryocytes generated from hiPS and hES cells in 3D and 2D culture using Combicult derived and published protocols: A. eh-iPS and iPS-SBi cells were encapsulated and differentiated following CombiCult derived protocols 4, 5, 16, 21 and 22 or using media conditions described in Feng et al (2014) (Lanza media). (i) The purity of generated megakaryocytes (CD41a$^+$/CD42b$^+$) was assessed by FACS analysis. (ii) The yield of mature MKs was assessed by flow cytometry using counting beads. (iii, iv) The efficiency of MK production from encapsulated hES Shef1 cells using differentiation protocols 5, 21 and 22 was assessed by FACS analysis. (v) Representative FACS scatter plots illustrating populations of hematopoetic cells (CD45$^+$) and megakaryoctes (CD45$^+$/CD41$^+$) following differentiation of SBI iPS and feeder-free episomal iPS cells, respectively in differentiation protocol 5. B. Expression of MPL gene (TPO receptor) in iPS-SBi (i, ii) and eh-iPS (iii, iv) cells differentiated by protocols 5 (i, iii) and 21 (ii, iv) was analyzed at 4 stages of differentiation by qPCR. C. Expression of four late genes associated with megakaryocyte differentiation and maturation was analysed by qPCR at four time-points (days 0, 4, 7 and 14). iPS-SBi (i, ii) and eh-iPS (iii, iv) cells were differentiated according to protocols 5 (i, iii) and 21 (ii, iv). All gene expression was normalised to internal control gene GAPDH. D. Evaluation of CombiCult derived MK protocols in the bead-free differentiation assay using collagen IV. (i) Cells were differentiated on plates coated with collagen IV using media conditions from protocols 4, 5, 16, 21, 22 and protocol published by Lanza droup and stained with anti CD41a (green) and anti CD42B (red) antibodies. (ii) Performance of CombiCult derived protocols on Collagen. Expression of CD41a and CD42b markers was analysed by FACS. E. FACS scatter plots demonstrating the efficiency of megakaryocyte protocol 5 in (i) static, well-based culture compared to (ii) large-scale suspension culture using the WAVE Bioreactor (ii).
Figure 3:
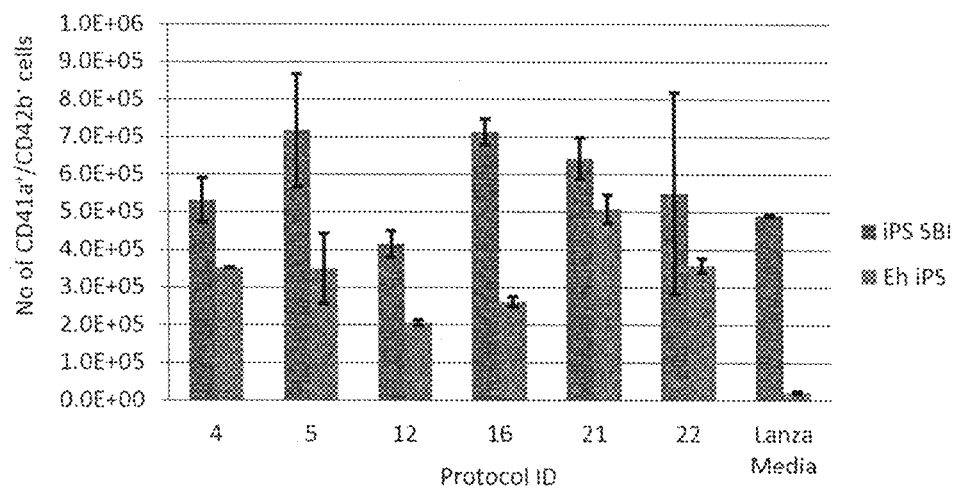
Figure 3:
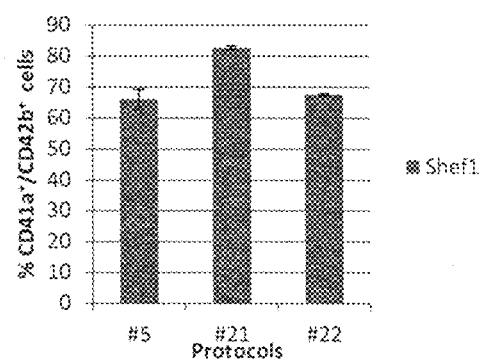
Figure 3:
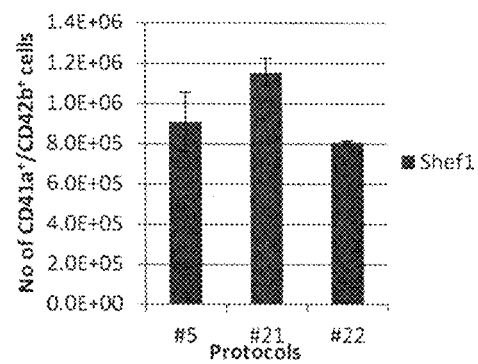
Figure 3:
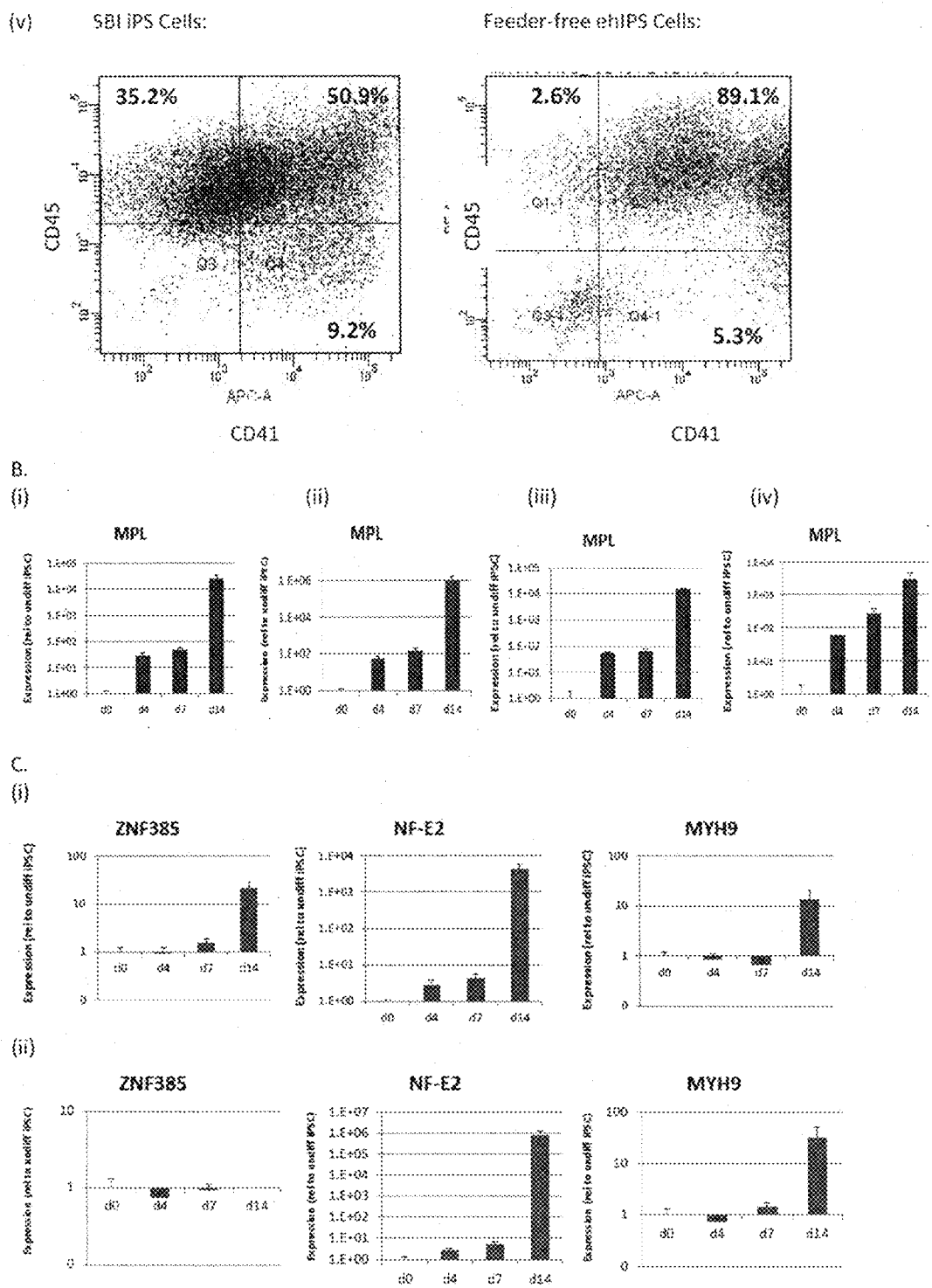
Figure 3:
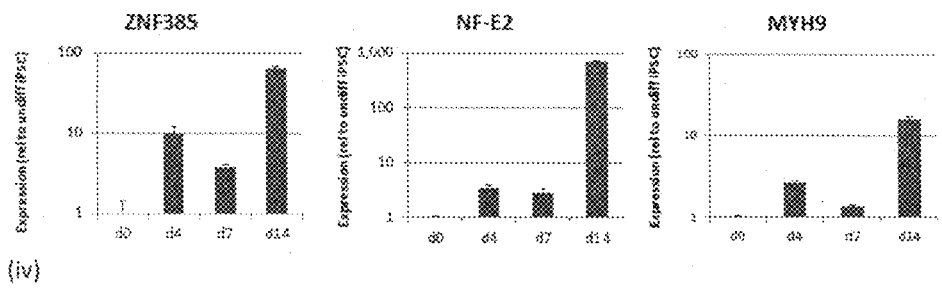
Figure 3:
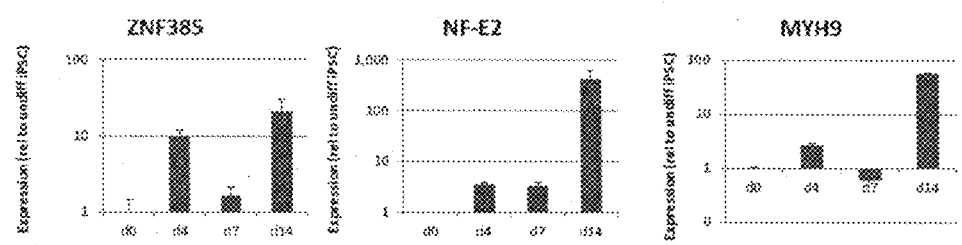
Figure 3:
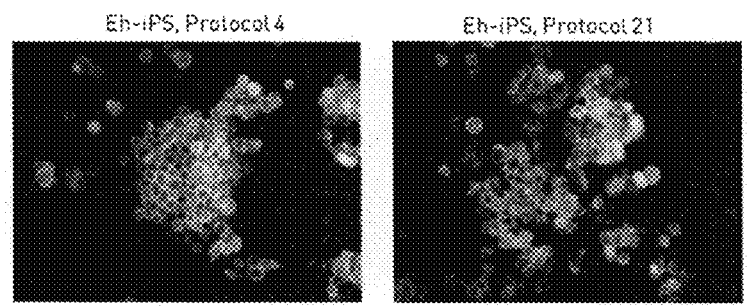
Figure 3:
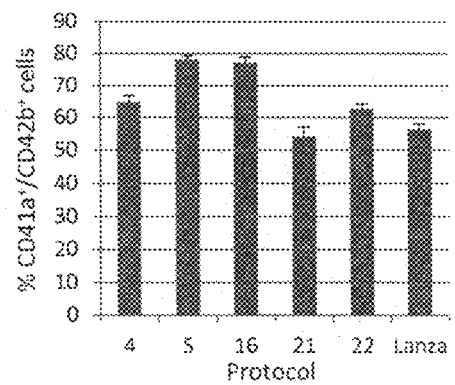
Figure 3:
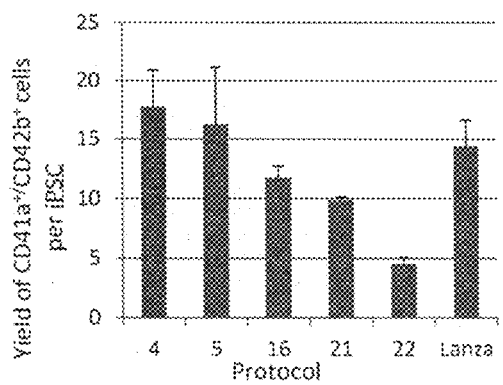
Figure 3:
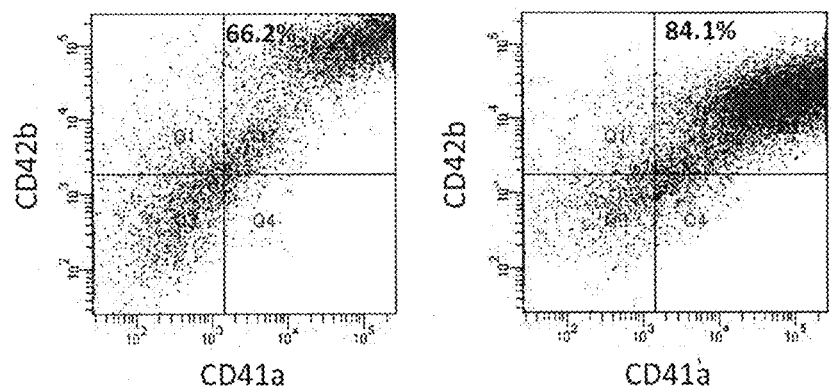

To verify that cells produced by the megakaryopoietic protocols were of the correct phenotype, qPCR analysis was performed at each stage of differentiation. At day 4, all RNA for cDNA synthesis was extracted from cells within the alginate beads as extrusion had not commenced yet. At days 7 and 14, however, all relevant RNA was extracted from cells extruded from the alginate beads. Gene expression at each stage was compared to undifferentiated iPS cells (day 0). The results are shown in FIG. 3*b*. Expression of MPL, the gene responsible for TPO receptor, which is a relatively early marker of megakaryocyte differentiation (Besancenot et al. 2014) was significantly upregulated at day 4 and again at day 14 (FIG. 3B). Expression of NF-E2 and MYH9, two genes associated specifically with megakaryocyte maturation and proplatelet formation (Maupin et al. 1994; Shivdasani 1996) were upregulated mostly at day 14 (FIG. 3C). This confirmed that day 14 cells were of the mature megakaryocyte phenotype.

Applicants had tested whether protocols that were developed for differentiating cells in alginate beads would work in conventional 2D system. In this assay feeder-free ehiPS cells were harvested enzymatically using Accutase and seeded onto tissue culture plates coated with collagen IV in Essential 8 media with 5 mM rock inhibitor. After sequential media changes at the same time intervals as before (d4, d7 and d11), cells were analysed at day 14 for the expression of CD45, CD41a and CD42b markers by flow cytometry. Efficiency of differentiation was compared to that achieved by a previously published protocol for feeder-free iPSC's, differentiated in a similarly monolayer-based manner (Feng et al, 2014). Applicants' results show that 2 out of 3 of the Combicult-derived protocols matched or surpassed the best presently known protocol (Lanza lab, published in 2015) in terms of yield of mature MKs (FIG. 3D).

Figure 4:
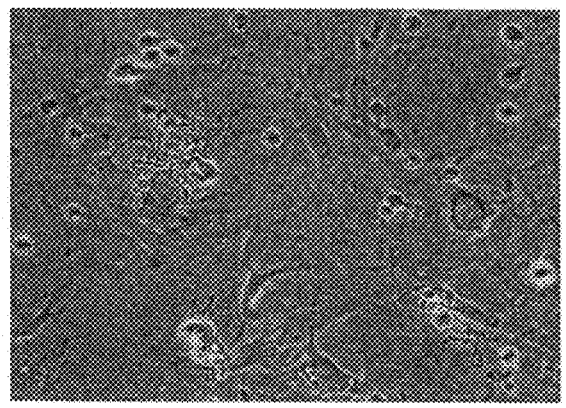
FIG. 4A-4C. Platelet production and activation: A. Platelet production following maturation of eh-iPS derived Megakaryocytes on uncoated plastic. (i) Mature megakaryocytes derived from eh-iPS cells form pro-platelets (bright field, objective ×20, arrows indicate areas of pro-platelet formation). (ii) iPS derived platelets were immunostained with CD41a and CD42b antibodies and analyzed by FACS. B. Platelet activation assay I: analysis of CD62P expression on the surface of activated platelets derived from eh-iPS cells (FACS analysis). (i) iPS derived platelets are gated on size using blood platelets. (ii) Platelets activated by addition of ADP (5 uM) or Thrombin (1 u/ml) show elevated level of CD62P expression. C. Platelets activation assay II: platelets spreading on slides coated with fibrinogen. Platelets were produced from mature MKs derived from eh-iPS by protocol 5 (i, ii) and protocol 21 (iii, iv). PF4-positive platelets were activated using ADP and Thrombin. Activated PF4-positive platelets spread (forming defined F-Actin stress fibres) upon contact with fibrinogen-coated plates (i, iii). BSA-coated plates were used as a negative control (activated platelets do not spread on BSA) (ii, iv). The seeding densities for both fibrinogen and BSA were the same. Scale bars=10 μm.
Figure 4:
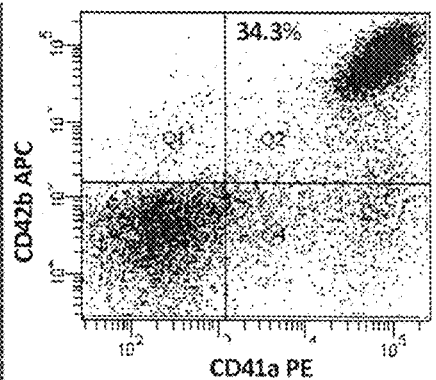
Figure 4:
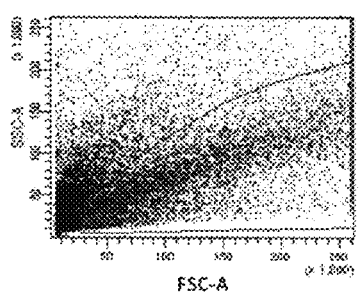
Figure 4:
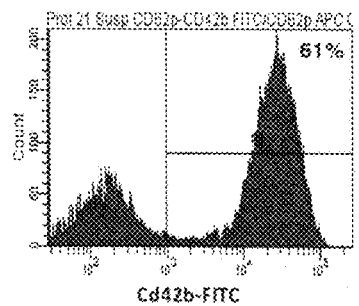
Figure 4:
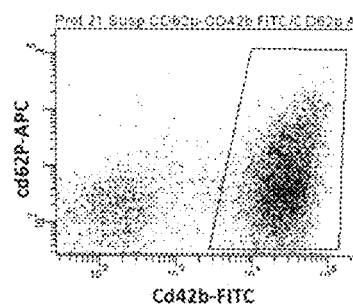
Figure 4:
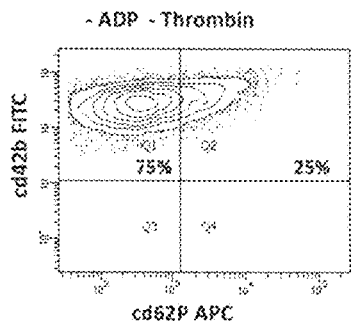
Figure 4:
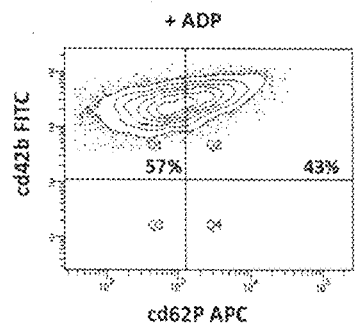
Figure 4:
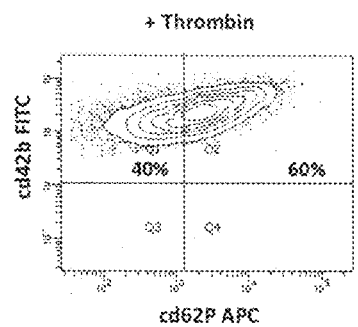
Figure 4:
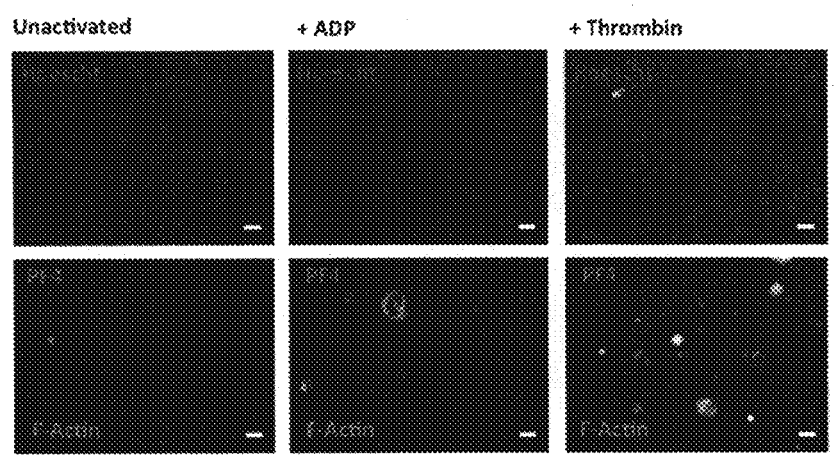
Figure 4:
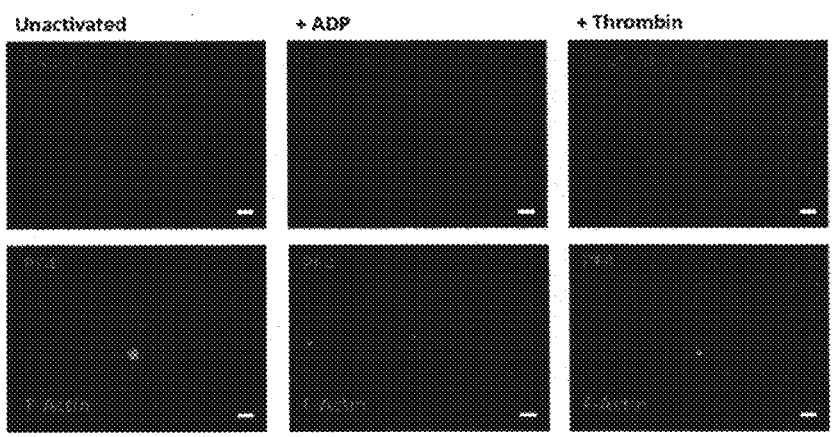
Figure 4:
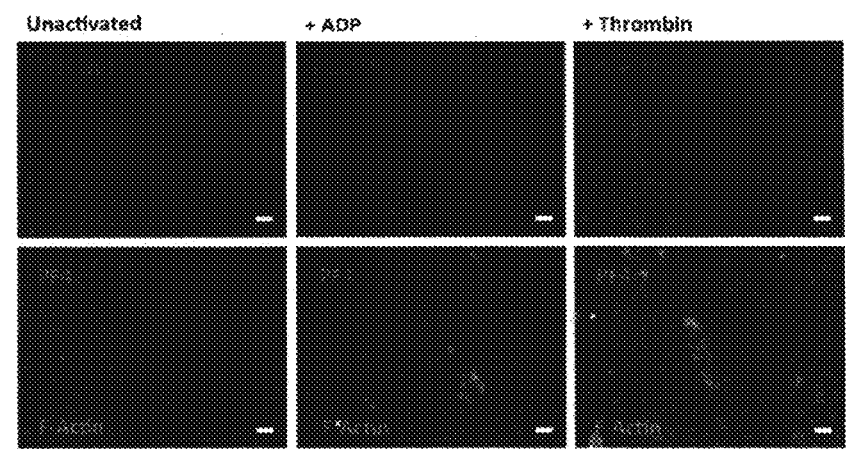
Figure 4:
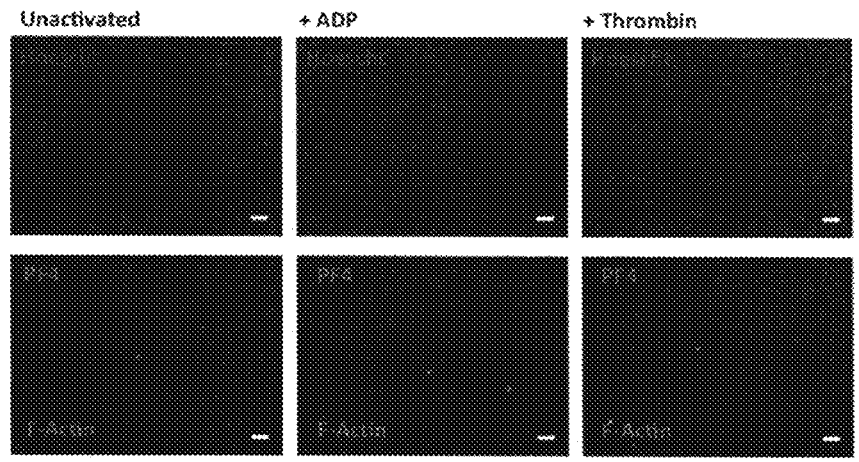

Megakaryocytes generated by new protocols using alginate beads were competent in their ability to produce platelets when cultured on OP9 feeder layers, Nanex scaffolds or untreated plastic. A further 4-5 days of culture was required for megakaryocytes to initiate platelet production. Platelets were isolated from media by differential centrifugation, immunostained with cd41a and cd42b antibodies and analyzed by flow cytometry using size gating on human blood platelets (FIG. 4A).

Functionality of hiPSC-derived platelets was assessed by a platelet activation assay that registered changes in expression of the adhesion protein P-selectin (cd62P) on the plasma membrane upon platelet activation. P-selectin plays a major role in leucocyte adhesion and regulation of homeostasis. It is stored in secretory granules of non-activated platelets and translocates quickly to the membrane following activation with agonists such as thrombin, type II collagen and ADP. Applicants differentiated eh-iPS-derived megakaryocytes according to protocol #5 followed by an additional 5 days in the final protocol #5 media in suspension plates and collected platelets in the presence of PGE1 and apyrase to prevent spontaneous platelet activation. Significant increases in the level of cd62P (P selectin) expression measured by flow cytometry on cd42b positive platelets following short incubation with ADP, Thrombin (FIG. 4B), collagen peptide or TRAP (data not shown) demonstrated that platelets derived from iPS cells by CombiCult protocols are functionally active.

Applicants had also tested platelets activity by means of a fibrinogen binding assay. PF4 antibody expression was used to characterise platelets, whilst the nuclear dye Hoescht was used to confirm that platelets did not contain nuclei. Applicants had compared the spreading ability of iPSC-derived platelets on slides coated with fibrinogen against a BSA negative control following activation with ADP, Thrombin (FIG. 4C) and collagen (data not shown). F-actin was used to visualise spreading. Applicants' results clearly show that platelets derived using protocols described earlier (protocols #5 and #21) bound and spread (forming characteristically defined, parallel F-actin fibres) to fibrinogen coated slides, upon stimulation by the activators tested. In contrast, platelets derived from the same protocols failed to bind (most were simply washed off) and spread on BSA coated slides (FIG. 4C).

In order to demonstrate the scalability of this novel alginate-based technology, alginate-encapsulated human ehiPS cells were seeded into a WAVE bioreactor (GE) and differentiated into megakaryocytes using Combicult protocol #5. A total of $1.68 \times 10^7$ cells were harvested from the bioreactor in 500 mL of medium (following filtration through a 70 um sieve to remove large aggregates and alginate beads). Approximately 84% of harvested cells were CD41a$^+$CD42b$^+$ mature megakaryocytes. These results demonstrate that the alginate-based technology, along with Combicult-derived protocols can be utilised as part of large-scale, suspension-based bioreactor systems.

TABLE 1

Media compositions used in Combicult megakaryocyte differentiation protocols:

|  | Protocol 4 | Protocol 5 | Protocol 12 | Protocol 16 |
|---|---|---|---|---|
| Day 1 | STEMUNE<br>BMP4 50 ng/ml<br>VEGF 50 ng/ml<br>bFGF 50 ng/ml | STEMUNE<br>BMP4 50 ng/ml<br>VEGF 50 ng/ml<br>bFGF 50 ng/ml | STEMUNE<br>BMP4 50 ng/ml<br>VEGF 50 ng/ml<br>bFGF 50 ng/ml | STEMUNE<br>BMP4 50 ng/ml<br>VEGF 50 ng/ml<br>bFGF 50 ng/ml |
| Day 4 | STEMUNE<br>BMP4 10 ng/ml<br>VEGF 10 ng/ml<br>bFGF 10 ng/ml<br>Ascorbic Acid 284 μM<br>BME<br>ETP 0.5 μM | STEMUNE<br>BMP4 10 ng/ml<br>VEGF 10 ng/ml<br>bFGF 10 ng/ml<br>Ascorbic Acid 284 μM<br>BME | STEMUNE<br>BMP4 10 ng/ml<br>VEGF 10 ng/ml<br>bFGF 10 ng/ml<br>Ascorbic Acid 284 μM<br>BME<br>ETP 0.5 μM | STEMUNE<br>BMP4 10 ng/ml<br>VEGF 10 ng/ml<br>bFGF 10 ng/ml<br>Ascorbic Acid 284 μM<br>BME<br>ETP 0.5 μM |
| Day 7 | STEMUNE<br>TPO 25 ng/ml<br>SCF 25 ng/ml<br>Flt3 25 ng/ml<br>IL3 10 ng/ml<br>Il6 10 ng/ml<br>Heparin 5 U/ml<br>IBET151 0.25 μM (24 h) | SFEM<br>TPO 50 ng/ml<br>SCF 50 ng/ml<br>Flt3 50 ng/ml<br>IL6 20 ng/ml<br>IL9 10 ng/ml<br>Heparin 5 U/ml<br>Valproic Acid 10 μM | STEMUNE<br>BMP4 50 ng/ml<br>VEGF 50 ng/ml<br>SCF 40 mg/ml<br>Flt3 40 ng/ml<br>TPO 50 ng/ml | SFEM<br>TPO 50 ng/ml<br>SCF 50 ng/ml<br>FR3 50 ng/ml<br>Il6 20 ng/ml<br>IL9 10 ng/ml<br>Heparin 5 U/ml<br>Valproic Acid 10 μM |
| Day 11 | SFEM<br>TPO 50 ng/ml<br>SCF 50 ng/ml<br>IL6 10 ng/ml<br>IL9 10 ng/ml<br>Arachidoic Acid 5 μM<br>ETP 0.5 μM<br>Nicotinamide 2.5 mM | SFEM<br>TPO 50 ng/ml<br>SCF 50 ng/ml<br>IL6 10 ng/ml<br>IL9 10 ng/ml<br>Arachidoic Acid 5 μM<br>ETP 0.5 μM<br>Nicotinamide 2.5 mM | SFEM<br>TPO 50 ng/ml<br>SCF 50 ng/ml<br>IL6 20 ng/ml<br>IL9 10 ng/ml<br>Heparin 5 U/ml<br>Valproic Acid 10 μM | SFEM<br>TPO 50 ng/ml<br>SCF 50 ng/ml<br>IL6 20 ng/ml<br>IL9 10 ng/ml<br>Heparin 5 U/ml<br>Valproic Acid 10 μM |

|  | Protocol 21 | Protocol 22 | Lanza |
|---|---|---|---|
| Day 1 | STEMUNE<br>BMP4 50 ng/ml<br>VEGF 50 ng/ml<br>bFGF 50 ng/ml | STEMUNE<br>BMP4 50 ng/ml<br>VEGF 50 ng/ml<br>bFGF 50 ng/ml | STEMspan ACF<br>BMP4 50 ng/ml<br>VEGF 50 ng/ml<br>bFGF 50 ng/ml |
| Day 4 | STEMUNE<br>BMP4 50 ng/ml<br>VEGF 50 ng/ml<br>bFGF 20 ng/ml<br>TPO 20 ng/ml<br>SCF 20 ng/ml<br>Valproic Acid 10 μM | STEMUNE<br>BMP4 10 ng/ml<br>VEGF 10 ng/ml<br>bFGF 10 ng/ml<br>Ascorbic Acid 284 μM<br>BME<br>ETP 0.5 μM | STEMspan ACF<br>BMP4 50 ng/ml<br>VEGF 50 ng/ml<br>bFGF 50 ng/ml |
| Day 7 | STEMUNE<br>SCF 20 ng/ml<br>Compound-P 500 nM<br>GPH40ag 100 nM<br>Metformin 2 mM<br>Heparin 5 U/ml | SFEM<br>TPO 50 ng/ml<br>SCF 50 ng/ml<br>Flt3 50 ng/ml<br>IL3 10 ng/ml<br>Il6 20 ng/ml<br>Heparin 5 U/ml<br>Scriptald 0.5 μM<br>TWS119 1 μM | STEM diff APEL<br>TPO 25 ng/ml<br>SCF 25 ng/ml<br>Flt3 25 ng/ml<br>IL3 10 ng/ml<br>Il6 10 ng/ml<br>Heparin 5 U/ml |

TABLE 1-continued

Media compositions used in Combicult megakaryocyte differentiation protocols:

| | | | |
|---|---|---|---|
| Day 11 | SFEM | SFEM | STEM diff APEL |
| | TPO 50 ng/ml | TPO 25 ng/ml | TPO 50 ng/ml |
| | SCF 50 ng/ml | SCF 50 ng/ml | SCF 25 ng/ml |
| | IL6 10 ng/ml | IL6 20 ng/ml | Flt3 25 ng/ml |
| | IL9 10 ng/ml | IL9 10 ng/ml | IL3 10 ng/ml |
| | Arachidoic Acid 5 μM | Heparin 5 U/ml | Il6 10 ng/ml |
| | ETP 0.5 μM | Valproic Acid 10 μM | Heparin 5 U/ml |
| | Nicotinamide 2.5 mM | | |

Example 4: Differentiation within Alginate Scaffolds Promotes Megakaryocyte Lineage Specification Applicants carried out another set of experiments demonstrating that in addition to providing an EB-free, feeder-free and highly scalable method for generation of hematopoietic progenitors, the encapsulation into alginate beads is specifically advantageous for differentiation into megakaryocyte lineage.

Figure 5:
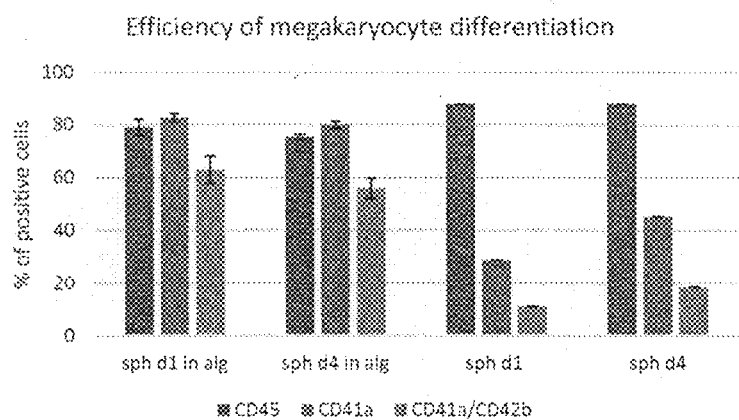
FIG. 5A-5C. Differentiation of encapsulated and non-encapsulated hESC spheroids: A. Efficiency of megakaryocyte differentiation for encapsulated and non-encapsulated spheroids at Day 15 of differentiation. B. Efficiency of macrophage differentiation in spheroid and spheroid/alginate cultures at Day 18 of differentiation. C. Polarisation of iPSC derived macrophages into M1 and M2 subtypes.
Figure 5:
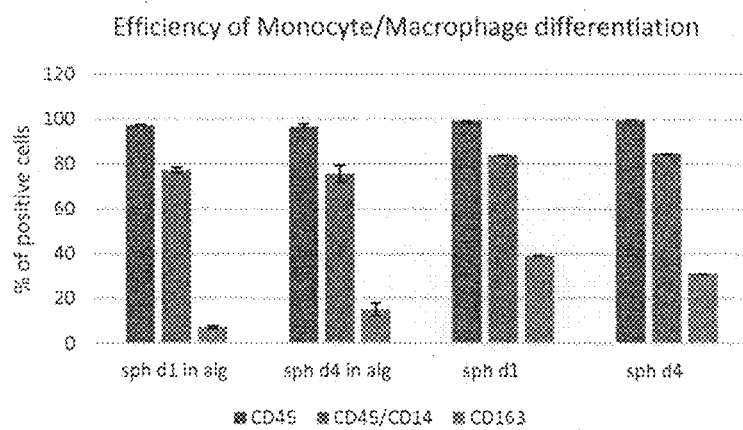
Figure 5:
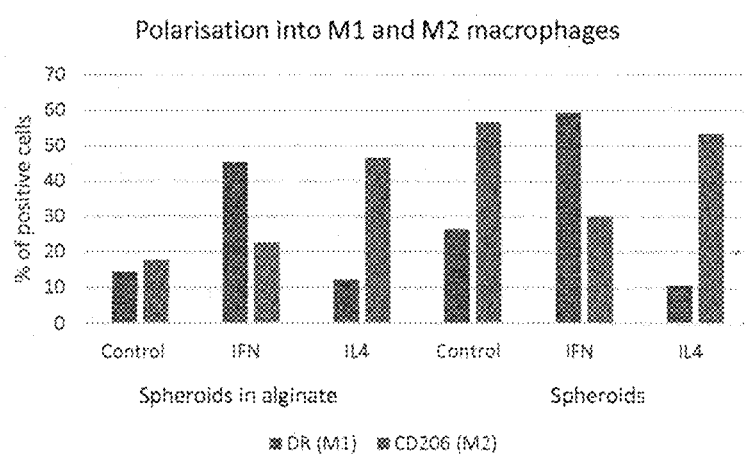

Applicants used a recently developed method of culturing hES and iPS cells as multicellular aggregates called spheroids (Takara Bio USA). In order to form spheroids, pluripotent stem cells were dissociated into a single cell suspension and then cultured on an orbital shaker for 24 hrs in Cellartis DEF-CS 500 Xeno-Free 3D Spheroid Culture Medium (Takara Bio USA). After 24 hours cells formed small aggregates, remained pluripotent and continued to grow into bigger spheroid structures. Applicants used aggregates from Day 1 and Day 4 of spheroid culture and either encapsulated them in alginate beads prior to differentiation or directly placed them into the first differentiation media for the megakaryocyte (protocol 5) or macrophage (protocol 2) lineages. Applicants had observed that both encapsulated and non-encapsulated spheroids generated CD45 positive hematopoietic cells with similar high efficiencies (80-90% of CD45 positive cells at Day 15 of differentiation). However the percentage of mature megakaryocytes was 6 times higher in populations of cells produced by encapsulated spheroids (63% vs 11% for Day 1 encapsulated spheroids) (FIG. 5 A). Analysis of differentiation into the monocyte/macrophage lineage didn't reveal any significant difference in the efficiency of monocyte differentiation between encapsulated and non-encapsulated spheroids (FIG. 5 B). Furthermore the population of hematopoietic cells generated from non-encapsulated spheroids contained a higher percentage of mature M2 macrophages (CD163+) (FIG. 5 B). Macrophages that were generated from non-encapsulated spheroids expressed high level of CD206, the marker for M2 macrophages, and were not responsive to treatment with IL4 while macrophages produced in alginate scaffolds could be successfully polarised with stimuli promoting both M1 (IFNγ) and M2 (IL4) phenotypes (FIG. 5 C).

These results indicate that the method of differentiation using alginate scaffolds gives additional advantages to differentiation into the megakaryocyte lineage. 3D alginate scaffolds provide a more physiologically relevant environment that is closer to developmental conditions in vivo. Applicants' results may reflect the way that hematopoietic cells emerge during development. It is known that macrophages emerge first during the primitive wave of hematopoiesis where some persist into adulthood whilst the developmental path of megakaryocytes is much more complex.

Example 5: Testing Alginate Hydrogels for Use in Hematopoietic Differentiation Protocols Two main criteria were used to select alginate gels for encapsulation and differentiation of pluripotent cells: (1) The hydrogel should form into round shaped beads with a diameter of 250-500 um, which should be stable in tissue culture media at 37° C.; (2) The composition and viscosity of hydrogel beads should be compatible with survival and proliferation of encapsulated pluripotent cells. Several alginate hydrogels from various suppliers were tested at a range of concentrations (1.5%-2.5%). Generally, alginate gels with concentrations lower than 1.5% either failed to form spherical beads during encapsulation or lost their shape upon cultivation. At concentrations higher than 2.5% most of the tested hydrogels were too viscous for the spraying and encapsulation process. Some hydrogels at higher concentrations formed high viscosity scaffolds that restricted proliferation/movement of differentiating cells and prevented extrusion of hematopoietic progenitors from the beads. Applicants had tested alginate preparations that passed the first requirement (formed round beads of correct size) in differentiation experiments using CombiCult-derived megakaryocyte differentiation protocols. Results demonstrating the efficiency of differentiation from feeder-dependent cell line iPS-SBI and feeder-free cell line eh-iPS into the megakaryocyte lineage in beads formed from different alginate formulations are summarised in Tables 2 and 3.

Alginate hydrogels used in the experiments:

Protanal: sodium alginate supplied by FMC BioPolymer

MVM: sodium alginate Pronova UP MVM supplied by NovaMatrix

MVG: sodium alginate Pronova UP MVG supplied by NovaMatrix

Sigma sodium alginate (BioReagent grade) 71238

TABLE 2 iPS-SBi differentiation into megakaryocyte lineage

| | Total Cells | % CD45 | % CD42b/CD41a |
|---|---|---|---|
| Protanal 2% | | | |
| Prot #4 | 4.00E+06 | 92.6 | 32.7 |
| Prot #5 | 5.64E+06 | 84.5 | 62.2 |
| Prot #16 | 3.71E+06 | 90.7 | 58.2 |
| Protanal 2.2% | | | |
| Prot #4 | 2.86E+06 | 89.4 | 38.3 |
| Prot #5 | 3.77E+06 | 82.7 | 65.8 |
| Prot #16 | 3.27E+06 | 88.5 | 57.7 |

TABLE 2-continued iPS-SBi differentiation into megakaryocyte lineage

|  | Total Cells | % CD45 | % CD42b/CD41a |
|---|---|---|---|
| MVG 2% | | | |
| Prot #4 | 2.80E+06 | 89.6 | 43.5 |
| Prot #5 | 2.82E+06 | 77.2 | 73.1 |
| Prot #16 | 1.43E+06 | 90.2 | 79.5 |

TABLE 3 eh-iPS differentiation into megakaryocyte lineage

|  | Total Cells | % CD45 | % CD42b/CD41a |
|---|---|---|---|
| Protanal 2% | | | |
| Prot #5 | 1.36E+06 | 58.7 | 41.4 |
| Prot #21 | 1.73E+06 | 48 | 33.0 |
| Prot #22 | 3.28E+05 | 86 | 37.2 |
| Protanal 2.2% | | | |
| Prot #5 | 2.21E+05 | 65.2 | 29.3 |
| Prot #21 | 3.99E+05 | 39.1 | 33.2 |
| Prot #22 | 4.73E+05 | 78.7 | 25.8 |
| Protanal 2.5% | | | |
| Prot #5 | 1.05E+06 | 65.2 | 27.2 |
| Prot #21 | 1.96E+06 | 39.1 | 27.0 |
| Prot #22 | 2.25E+05 | 78.7 | 23.4 |
| MVM 1.5% | | | |
| Prot #5 | 5.46E+05 | 66.2 | 39.1 |
| Prot #21 | 6.59E+05 | 28.9 | 20.0 |
| Prot #22 | 3.76E+05 | 76.8 | 35.0 |
| MVG 2% | | | |
| Prot #22 | 1.64E+05 | 88.4 | 51.5 |
| Sigma 1.7% | | | |
| Prot #5 | 7.64E+05 | 91.65 | 72.2 |
| Sigma 2% | | | |
| Prot #5 | 8.29E+04 | 86.3 | 65.2 |

The invention is further described by the following numbered paragraphs:

1. A hydrogel capsule comprising a stem cell core that has been induced to differentiate into a hematopoietic lineage cell.

2. A hydrogel capsule according to paragraph 1, wherein the hematopoietic lineage cell is extruding from the hydrogel capsule.

3. A hydrogel capsule according to paragraph 1 or paragraph 2, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

4. A hydrogel capsule according to any preceding paragraph, wherein the stem cell core is a clump of stem cells or a spheroid.

5. A hydrogel capsule according to any preceding paragraph, wherein the hydrogel comprises an alginate.

6. A method for producing a hematopoietic lineage cell, comprising the steps of:
   a) encapsulating a stem cell core in a hydrogel; and
   b) exposing the encapsulated stem cell core to a culture condition which promotes differentiation of the stem cell core into the hematopoietic lineage cell.

7. A method according to paragraph 6, further comprising the steps of:
   a) changing the culture condition to a different culture condition which further promotes differentiation of the stem cell into the hematopoietic lineage cell; and optionally
   b) repeating step a) with further different culture conditions which further promote differentiation of the stem cell into the hematopoietic lineage cell.

8. A method according to paragraph 6 or paragraph 7, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

9. A method according to any of paragraphs 6 to 8, comprising an initial culture condition, and first, second, and third different culture conditions.

10. A method according to paragraph 9, wherein the initial culture condition comprises a medium comprising:
    a) a hematopoietic stem cell expansion medium; and
    b) 50 ng/ml of each of BMP4, VEGF, and bFEF;
    the first different culture condition comprises a medium comprising:
    a) a hematopoietic stem cell expansion medium;
    b) 10 ng/ml of each of BMP4, VEGF, and bFEF;
    c) 284 μM ascorbic acid; and
    d) 0.1 mM βME;
    the second different culture condition comprises a medium comprising:
    a) SFEM;
    b) 50 ng/ml of each of TPO, SCF, and Flt3;
    c) 20 ng/ml of IL6;
    d) 10 ng/ml of IL9;
    e) 5 U/ml of heparin; and
    f) 10 μM of Valproic acid;
    and the third different culture condition comprises a medium comprising:
    a) SFEM;
    b) 50 ng/ml of each of TPO and SCF;
    c) 10 ng/ml of each of IL6 and IL9;
    d) 5 μM of Arachidoic acid;
    e) 0.5 μM of ETP; and
    f) 2.5 mM nicotinamide.

11. A method according to paragraph 9, wherein the initial culture condition comprises a medium comprising:
    a) a hematopoietic stem cell expansion medium; and
    b) 50 ng/ml of each of BMP4, VEGF, and bFEF;
    the first different culture condition comprises a medium comprising:
    a) a hematopoietic stem cell expansion medium;
    b) 50 ng/ml of each of BMP4 and VEGF;
    c) 20 ng/ml of each of bFEF, TPO, and SCF; and
    d) 10 μM Valproic acid;
    the second different culture condition comprises a medium comprising:
    a) a hematopoietic stem cell expansion medium;
    b) 20 ng/ml of SCF;
    c) 500 nM of Compound-P;
    d) 100 nM of GPR40ag;
    e) 2 mM of Metformin; and
    f) 5 U/ml of heparin;
    and the third different culture condition comprises a medium comprising:
    a) SFEM;
    b) 50 ng/ml of each of TPO and SCF;
    c) 10 ng/ml of each of IL6 and IL9;

d) 5 µM of Arachidoic acid;
e) 0.5 µM of ETP; and
f) 2.5 mM nicotinamide.

12. A method according to any of paragraphs 9 to 11, wherein the day on which the encapsulated stem cell is exposed to the initial culture condition is day 1, and the encapsulated stem cell is exposed to the first different culture condition on day 3 or day 4, to the second different culture condition on day 7, and to the third different culture condition on day 11.

13. A method according to any of paragraphs 6 to 12, further comprising the step of separating one or more hematopoietic lineage cells from the encapsulated stem cells.

14. A method according to any of paragraphs 6 to 13, wherein at least one culture condition is feeder-free.

15. A method according to any of paragraphs 6 to 14, wherein at least one culture condition does not comprise any of a conditioned medium, serum, or a ROCK inhibitor.

16. A method according to any of paragraphs 6 to 15, wherein the hydrogel comprises an alginate.

17. A method according to any of paragraphs 6 to 16, wherein the stem cell core is a spheroid.

18. A composition comprising:
a) a hydrogel capsule comprising a stem cell; and
b) a hematopoietic lineage cell.

19. A composition according to paragraph 18, wherein the hematopoietic lineage cell is located outside of the hydrogel capsule.

20. A composition according to paragraph 18 or paragraph 19, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

21. A vessel, preferably a bioreactor, containing one or more hydrogel capsules according to any of paragraphs 1 to 5, or containing a composition according to any of paragraphs 18 to 20.

22. Use of a vessel according to paragraph 21 in a method for producing a hematopoietic lineage cell.

23. Use of a vessel according to paragraph 21 or paragraph 22, wherein the method is a method according to any of paragraphs 6 to 17.

24. Use of a vessel according to any of paragraphs 21 to 23, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

25. Use of a hydrogel capsule according to any of paragraphs 1 to 5 in a method for producing a hematopoietic lineage cell.

26. Use of a hydrogel capsule according to paragraph 25, wherein the method is a method according to any of 6 to 17.

27. Use of a hydrogel capsule according to paragraph 25 or paragraph 26, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for producing a hematopoietic lineage cell, comprising the steps of:
   a) encapsulating a stem cell core in a hydrogel; and
   b) exposing the encapsulated stem cell core to a culture condition which promotes differentiation of the stem cell core into the hematopoietic lineage cell;
   wherein the hematopoietic lineage cell is extruding or extruded from the hydrogel capsule; and
   wherein the extruding or extruded cell is initially attached to the capsule.

2. A method according to claim 1, further comprising the steps of:
   a) changing the culture condition to a different culture condition which further promotes differentiation of the stem cell into the hematopoietic lineage cell; and optionally
   b) repeating step a) with further different culture conditions which further promote differentiation of the stem cell into the hematopoietic lineage cell.

3. A method according to claim 1, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

4. A method according to claim 1, comprising an initial culture condition, and first, second, and third different culture conditions.

5. A method according to claim 4, wherein the initial culture condition comprises a medium comprising:
   a) a hematopoietic stem cell expansion medium; and
   b) 50 ng/ml of each of BMP4, VEGF, and bFEF;
   the first different culture condition comprises a medium comprising:
   a) a hematopoietic stem cell expansion medium;
   b) 10 ng/ml of each of BMP4, VEGF, and bFEF;
   c) 284 µM ascorbic acid; and
   d) 0.1 mM βME;
   the second different culture condition comprises a medium comprising:
   a) SFEM;
   b) 50 ng/ml of each of TPO, SCF, and Flt3;
   c) 20 ng/ml of IL6;
   d) 10 ng/ml of IL9;
   e) 5 U/ml of heparin; and
   f) 10 µM of Valproic acid;
   and the third different culture condition comprises a medium comprising:
   a) SFEM;
   b) 50 ng/ml of each of TPO and SCF;
   c) 10 ng/ml of each of IL6 and IL9;
   d) 5 µM of Arachidoic acid;
   e) 0.5 µM of ETP; and
   f) 2.5 mM nicotinamide.

6. A method according to claim 4, wherein the initial culture condition comprises a medium comprising:
   a) a hematopoietic stem cell expansion medium; and
   b) 50 ng/ml of each of BMP4, VEGF, and bFEF;
   the first different culture condition comprises a medium comprising:
   a) a hematopoietic stem cell expansion medium;
   b) 50 ng/ml of each of BMP4 and VEGF;

c) 20 ng/ml of each of bFEF, TPO, and SCF; and
d) 10 µM Valproic acid;
the second different culture condition comprises a medium comprising:
a) a hematopoietic stem cell expansion medium;
b) 20 ng/ml of SCF;
c) 500 nM of Compound-P;
d) 100 nM of GPR40ag;
e) 2 mM of Metformin; and
f) 5 U/ml of heparin;
and the third different culture condition comprises a medium comprising:
a) SFEM;
b) 50 ng/ml of each of TPO and SCF;
c) 10 ng/ml of each of IL6 and IL9;
d) 5 µM of Arachidoic acid;
e) 0.5 µM of ETP; and
f) 2.5 mM nicotinamide.

7. A method according to claim 4, wherein the day on which the encapsulated stem cell is exposed to the initial culture condition is day 1, and the encapsulated stem cell is exposed to the first different culture condition on day 3 or day 4, to the second different culture condition on day 7, and to the third different culture condition on day 11.

8. A method according to claim 1, further comprising the step of separating one or more hematopoietic lineage cells from the encapsulated stem cells.

9. A method according to claim 1, wherein at least one culture condition is feeder-free.

10. A method according to claim 1, wherein at least one culture condition does not comprise any of a conditioned medium, serum, or a ROCK inhibitor.

11. A method according to claim 1, wherein the hydrogel comprises an alginate.

12. A method according to claim 1, wherein the stem cell core is a spheroid.

13. A composition comprising:
a) a hydrogel capsule; and
b) a hematopoietic lineage cell extruding or extruded from the hydrogel capsule;
wherein the extruding or extruded cell is initially attached to the capsule.

14. A composition according to claim 13, wherein the hematopoietic lineage cell is located outside of the hydrogel capsule.

15. A composition according to claim 13, wherein the hematopoietic lineage cell is a hemogenic precursor cell, a multipotent hematopoietic stem cell, a multipotent hematopoietic progenitor cell, a common myeloid precursor, a common lymphoid precursor, a megakaryocyte, an erythrocyte, a T-lymphocyte, a B-lymphocyte, a natural killer cell, a monocyte, a macrophage, or a platelet.

16. A vessel containing a composition according to claim 13.

17. The vessel of claim 16, wherein the vessel is a bioreactor.

* * * * *